(12) United States Patent
Miyake et al.

(10) Patent No.: US 11,827,586 B2
(45) Date of Patent: Nov. 28, 2023

(54) METHOD FOR PRODUCING AMINO ACID AMINOALKYL ESTER OR INORGANIC ACID SALT THEREOF

(71) Applicant: ASAHI KASEI KABUSHIKI KAISHA, Tokyo (JP)

(72) Inventors: Nobuhisa Miyake, Tokyo (JP); Kazuhiro Takagaki, Tokyo (JP); Tsubasa Uematsu, Tokyo (JP); Koichi Nakaoka, Tokyo (JP); Masaaki Shinohata, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 67 days.

(21) Appl. No.: 17/052,541

(22) PCT Filed: May 15, 2019

(86) PCT No.: PCT/JP2019/019358
§ 371 (c)(1),
(2) Date: Nov. 3, 2020

(87) PCT Pub. No.: WO2019/221192
PCT Pub. Date: Nov. 21, 2019

(65) Prior Publication Data
US 2021/0253517 A1    Aug. 19, 2021

(30) Foreign Application Priority Data

May 15, 2018   (JP) ................. 2018-094173

(51) Int. Cl.
C07C 269/06    (2006.01)
C07C 227/18    (2006.01)
(Continued)

(52) U.S. Cl.
CPC .......... C07C 269/06 (2013.01); C07C 227/18 (2013.01); C07C 249/02 (2013.01);
(Continued)

(58) Field of Classification Search
None
See application file for complete search history.

(56) References Cited

U.S. PATENT DOCUMENTS 5,113,009 A    5/1992  Ajioke et al.
6,399,601 B1   6/2002  Du Bois
(Continued)

FOREIGN PATENT DOCUMENTS

CN    106316870 A    1/2017
EP       0544205 A2   6/1993
(Continued)

OTHER PUBLICATIONS

"Hydrocarbons" IUPAC. Compendium of Chemical Terminology, 2nd ed. (the "Gold Book"). Compiled by A. D. McNaught and A. Wilkinson. Blackwell Scientific Publications, Oxford (1997). Online version (2019-) created by S. J. Chalk. ISBN 0-9678550-9-8. https://doi.org/10.1351/goldbook. (Year: 1997).*

(Continued)

Primary Examiner — Amy C Bonaparte
(74) Attorney, Agent, or Firm — Morgan, Lewis & Bockius LLP

(57) ABSTRACT

The present invention provides a method for producing an amino acid aminoalkyl ester or an inorganic acid salt thereof by reacting a compound represented by general formula (I) shown below or a compound represented by general formula (III) shown below, or a salt thereof, and at least one compound selected from the group consisting of compounds represented by general formula (IV-I) shown below, compounds represented by general formula (IV-II) shown below, compounds represented by general formula (IV-III) shown below and compounds represented by general formula (IV-IV) shown below, or an inorganic acid salt thereof.

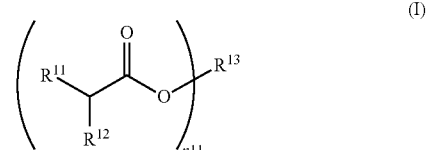

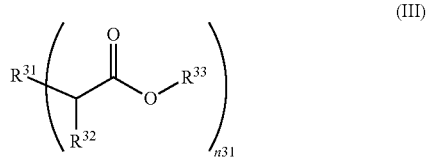

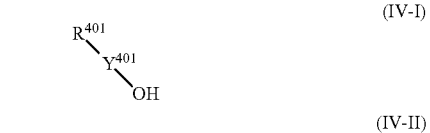

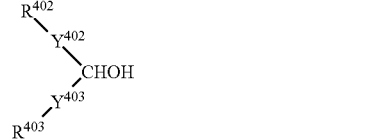

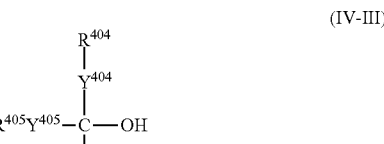

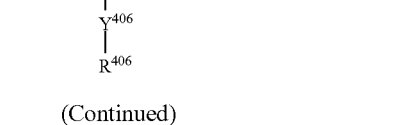

(Continued)

-continued $$\begin{array}{c} R^{407} \\ | \\ Y^{407} \\ | \\ R^{408}-Y^{408}-C-Y^{4010} \\ | \quad \quad \diagdown R^{4010} \\ Y^{409} \\ | \\ R^{409} \end{array} \quad (IV\text{-}IV)$$

5 Claims, No Drawings

(51) Int. Cl.
| | |
|---|---|
| *C07C 249/02* | (2006.01) |
| *C07C 273/18* | (2006.01) |
| *C07C 229/08* | (2006.01) |
| *C07C 229/24* | (2006.01) |
| *C07C 229/26* | (2006.01) |
| *C07C 229/36* | (2006.01) |
| *C07C 251/16* | (2006.01) |
| *C07C 271/48* | (2006.01) |
| *C07C 275/10* | (2006.01) |

(52) U.S. Cl.
CPC .......... *C07C 273/18* (2013.01); *C07C 229/08* (2013.01); *C07C 229/24* (2013.01); *C07C 229/26* (2013.01); *C07C 229/36* (2013.01); *C07C 251/16* (2013.01); *C07C 271/48* (2013.01); *C07C 275/10* (2013.01)

(56) References Cited

U.S. PATENT DOCUMENTS

| | | | |
|---|---|---|---|
| 2005/0192460 A1* | 9/2005 | Pascaly ................. | C07C 227/18 8/405 |
| 2009/0325980 A1* | 12/2009 | Meerpoel ............. | C07D 211/58 546/205 |
| 2015/0197483 A1 | 7/2015 | Harrington et al. | |
| 2020/0048403 A1 | 2/2020 | Miyake et al. | |
| 2021/0253517 A1* | 8/2021 | Miyake ................. | C07C 273/18 |

FOREIGN PATENT DOCUMENTS

| | | | |
|---|---|---|---|
| JP | S53-135931 A | 11/1978 | |
| JP | S55-105649 A | 8/1980 | |
| JP | S61-053248 A | 3/1986 | |
| JP | 02-256653 A | 10/1990 | |
| JP | 05-148199 A | 6/1993 | |
| JP | 2000-247938 A | 9/2000 | |
| JP | 2001-131181 A | 5/2001 | |
| JP | 2001-181246 A | 7/2001 | |
| JP | 2003-252840 A | 9/2003 | |
| JP | 2010-507615 A | 3/2010 | |
| WO | 2008/049806 A1 | 5/2008 | |
| WO | 2012/106588 A2 | 8/2012 | |
| WO | WO-2017099822 A1 * | 6/2017 | ............ A61K 31/66 |
| WO | 2018/070540 A1 | 4/2018 | |

OTHER PUBLICATIONS

"Isopropyl alcohol" Density, downloaded from https://pubchem.ncbi.nlm.nih.gov/compound/Isopropyl-alcohol#section=Density&fullscreen=true on Apr. 1, 2022 (Year: 2022).*
EDC•HCl, (downloaded from https://www.chembk.com/en/chem/EDC%C2%B7HCl on Sep. 15, 2022) (Year: 2022).*
Wright ("Convenient Preparations of t-Butyl Esters and Ethers from t-Butanol" Tetrahedron Letters, 38(42), 1997, p. 7345-7348) (Year: 1997).*
Hydrochloric acid (35%, Technical, downloaded from https://in.vwr.com/store/product/707437/hydrochloric-acid-35-technical on Sep. 15, 2022) (Year: 2022).*
P-Toluenesulfonic acid monohydrate ("Physical Description", downloaded from https://pubchem.ncbi.nlm.nih.gov/compound/p-Toluenesulfonic-acid-monohydrate#section=Physical-Description&fullscreen=true on Mar. 9, 2023) (Year: 2023).*
Benzene ("Density", downloaded from https://pubchem.ncbi.nlm.nih.gov/compound/Benzene#section=Density&fullscreen=true on Mar. 9, 2023). (Year: 2023).*
Acetic Acid ("Boiling Point", downloaded from https://pubchem.ncbi.nlm.nih.gov/compound/176#section=Boiling-Point&fullscreen=true on Mar. 9, 2023) (Year: 2023).*
European Search Report dated May 27, 2021 issued in European Application No. 19803769.9.
Written Opinion issued in corresponding International Patent Application No. PCT/JP2019/019358, dated Aug. 20, 2019.
Edited by the Chemical Society of Japan, The fourth series of experimental chemistry, 22, Organic Synthesis IV-acid, amino acid, peptide-, Maruzen Inc., Nov. 30, 1992, pp. 43-44 (with partial translation).
Hasan et al., "Five-membered rings, I. The reaction of 2-methyl-2-oxazoline with phthalimidoacetyl chloride", Canadian Journal of Chemistry, 1967, vol. 45, No. 17, pp. 2000-2002.
Schmidt et al., "Synthetic Strategies for the Modification of Diclofenac", Synlett, 2017, vol. 28, No. 15, pp. 1984-1989.
International Search Report issued in corresponding International Patent Application No. PCT/JP2019/019358, dated Aug. 20, 2019.

* cited by examiner

METHOD FOR PRODUCING AMINO ACID AMINOALKYL ESTER OR INORGANIC ACID SALT THEREOF

TECHNICAL FIELD

The present invention relates to a method for producing an amino acid aminoalkyl ester or an inorganic acid salt thereof.

Priority is claimed on Japanese Patent Application No. 2018-094173, filed May 15, 2018, the content of which is incorporated herein by reference.

BACKGROUND ART

One known method for producing an amino acid aminoalkyl ester or an inorganic acid salt thereof is a method in which an amino acid or a salt thereof and an amino alcohol or a salt thereof are subjected to an esterification reaction in the presence of hydrogen chloride and an organic solvent. In this reaction system, because the reaction tends to proceed poorly in the latter stages of the reaction, with a low conversion and reaction rate, a method has been proposed in which following supply of hydrogen chloride gas to the reaction system, an organic solvent is supplied to the reaction system, and the water produced by the reaction is removed (for example, see Patent Document 1).

PRIOR ART LITERATURE

Patent Document

Patent Document 1: Japanese Unexamined Patent Application, First Publication No. 2003-252840

SUMMARY OF INVENTION

Problems to be Solved by the Invention

However, in the method disclosed in Patent Document 1, because hydrogen chloride is used as a catalyst, hydrogen chloride gas is distilled off together with the water (steam) produced in the reaction, leading to the possibility of corrosion of the reaction container and lines.

The present invention has been developed in light of the above circumstances, and provides a method that can produce an amino acid aminoalkyl ester or an inorganic acid salt thereof in high yield without acid distillation.

Means for Solving the Problems

In other words, the present invention relates to the following aspects.

[1] A method for producing an amino acid aminoalkyl ester or an inorganic acid salt thereof by reacting:

a compound represented by general formula (I) shown below or a compound represented by general formula (III) shown below, or a salt thereof, and at least one compound selected from the group consisting of compounds represented by general formula (IV-I) shown below, compounds represented by general formula (IV-II) shown below, compounds represented by general formula (IV-III) shown below and compounds represented by general formula (IV-IV) shown below, or an inorganic acid salt thereof.

[Chemical formula 1]

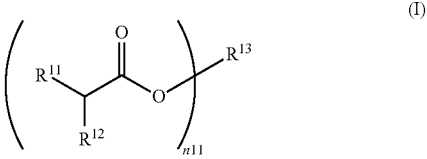

(In general formula (I), $R^{11}$ represents a hydrogen atom, a monovalent aliphatic hydrocarbon group of at least 1 but not more than 10 carbon atoms which may have a substituent, or a monovalent aromatic cyclic group of at least 6 but not more than 10 carbon atoms which may have a substituent. The substituent is at least one group selected from the group consisting of monovalent aliphatic hydrocarbon groups of at least 1 but not more than 10 carbon atoms, monovalent aromatic cyclic groups of at least 6 but not more than 10 carbon atoms, halogeno groups, alkoxy groups, thioalkyl groups, a primary amino group ($—NH_2$), a carboxyl group, a carbamide group ($—NHCONH_2$), groups represented by general formula (II-1) shown below, groups represented by general formula (II-2) shown below, groups represented by general formula (II-3) shown below, and groups represented by general formula (II-4) shown below. $R^{12}$ represents at least one group selected from the group consisting of an amino group, a carbamide group ($—NHCONH_2$), groups represented by general formula (II-1) shown below, groups represented by general formula (II-2) shown below, and groups represented by general formula (II-3) shown below. $R^{13}$ represents a hydrogen atom or an n11-valent organic group. Further, n11 is an integer of at least 1 but not more than 4.)

[Chemical formula 2]

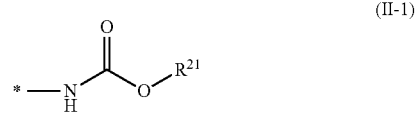

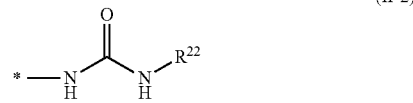

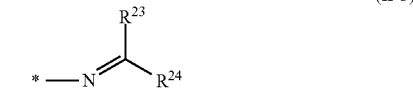

(In general formula (II-1), $R^{21}$ represents a monovalent aliphatic hydrocarbon group of at least 1 but not more than 10 carbon atoms which may have a substituent, or a monovalent aromatic cyclic group of at least 6 but not more than 10 carbon atoms which may have a substituent.

In general formula (II-2), $R^{22}$ represents a monovalent organic group.

In general formula (II-3), each of $R^{23}$ and $R^{24}$ independently represents a monovalent aliphatic hydrocarbon group of at least 1 but not more than 10 carbon atoms which may have a substituent, or a monovalent aromatic cyclic group of at least 6 but not 10 more than 10 carbon atoms which may have a substituent.

In general formula (II-4), $R^{25}$ represents a hydrogen atom or a monovalent organic group.)

[Chemical formula 3]

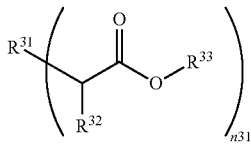

(III)

(In general formula (III), n31 is an integer of at least 2 but not more than 4. $R^{31}$ represents an n31-valent aliphatic hydrocarbon group of at least 1 but not more than 10 carbon atoms which may have a substituent, or an n31-valent aromatic cyclic group of at least 6 but not more than 10 carbon atoms which may have a substituent. The substituent is at least one group selected from the group consisting of monovalent aliphatic hydrocarbon groups of at least 1 but not more than 10 carbon atoms, monovalent aromatic cyclic groups of at least 6 but not more than 10 carbon atoms, halogeno groups, alkoxy groups, thioalkyl groups, a primary amino group (—$NH_2$), a carboxyl group, a carbamide group (—$NHCONH_2$), groups represented by general formula (II-1) shown above, groups represented by general formula (II-2) shown above, groups represented by general formula (II-3) shown above, and groups represented by general formula (II-4) shown above. $R^{32}$ represents at least one group selected from the group consisting of an amino group, a carbamide group (—$NHCONH_2$), groups represented by general formula (II-1) shown above, groups represented by general formula (II-2) shown above, and groups represented by general formula (II-3) shown above. $R^{33}$ represents a hydrogen atom or a monovalent organic group.)

[Chemical formula 4]

(IV-I)

(In general formula (IV-I), $Y^{401}$ represents a divalent aliphatic hydrocarbon group of at least 1 but not more than 10 carbon atoms or a divalent aromatic cyclic group of at least 6 but not more than 10 carbon atoms. $R^{401}$ represents at least one group selected from the group consisting of an amino group, a carbamide group (—$NHCONH_2$), groups represented by general formula (II-1) shown above, groups represented by general formula (II-2) shown above, groups represented by general formula (II-3) shown above, and groups represented by general formula (II-4) shown above.)

[Chemical formula 5]

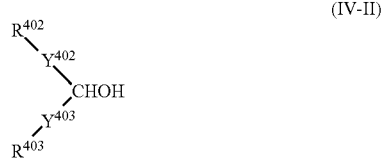

(IV-II)

(In general formula (IV-II), each of $Y^{402}$ and $Y^{403}$ independently represents a divalent aliphatic hydrocarbon group of at least 1 but not more than 10 carbon atoms or a divalent aromatic cyclic group of at least 6 but not more than 10 carbon atoms. Each of $R^{402}$ and $R^{403}$ independently represents at least one group selected from the group consisting of a hydrogen, an amino group, a carbamide group (—$NHCONH_2$), groups represented by general formula (II-1) shown above, groups represented by general formula (II-2) shown above, groups represented by general formula (II-3) shown above, and groups represented by general formula (II-4) shown above.)

[Chemical formula 6]

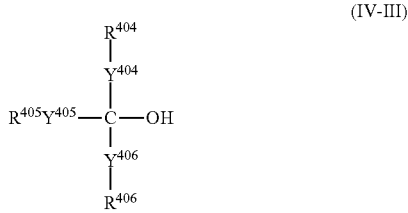

(IV-III)

(In general formula (IV-III), each of $Y^{404}$, $Y^{405}$ and $Y^{406}$ independently represents a divalent aliphatic hydrocarbon group of at least 1 but not more than 10 carbon atoms or a divalent aromatic cyclic group of at least 6 but not more than 10 carbon atoms. Each of $R^{404}$, $R^{405}$ and $R^{406}$ independently represents at least one group selected from the group consisting of a hydrogen, an amino group, a carbamide group (—$NHCONH_2$), groups represented by general formula (II-1) shown above, groups represented by general formula (II-2) shown above, groups represented by general formula (II-3) shown above, and groups represented by general formula (II-4) shown above.)

[Chemical formula 7]

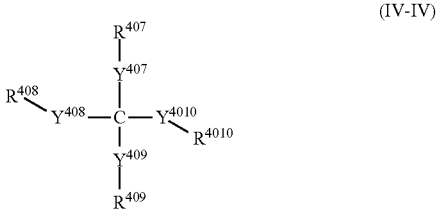

(IV-IV)

(In general formula (IV-IV), each of $Y^{407}$, $Y^{408}$, $Y^{409}$ and $Y^{4010}$ independently represents a divalent aliphatic hydrocarbon group of at least 1 but not more than 10 carbon atoms or a divalent aromatic cyclic group of at least 6 but not more than 10 carbon atoms. At least one of $R^{407}$, $R^{408}$, $R^{409}$ and $R^{4010}$ represents a hydroxyl group, and each of the others represents at least one group selected from the group consisting of a hydrogen, an amino group, a carbamide group (—NHCONH$_2$), groups represented by general formula (II-1) shown above, groups represented by general formula (II-2) shown above, groups represented by general formula (II-3) shown above, and groups represented by general formula (II-4) shown above.)

[2] The method according to [1], wherein the reaction is conducted in the presence of at least one acid catalyst selected from the group consisting of organic acids and inorganic acids having a normal boiling point of 0° C. or higher.

[3] The method according to [1] or [2], wherein the compound represented by general formula (I) is at least one amino acid selected from the group consisting of lysine, glutamic acid, methionine, glycine, phenylalanine, asparagine, alanine, leucine, isoleucine, and valine.

[4] The method according to [2] or [3], wherein the inorganic acid used as an acid catalyst is at least one acid selected from the group consisting of sulfuric acid, phosphoric acid, nitric acid and boric acid.

[5] The method according to any one of [2] to [4], wherein an acid that forms a salt with the compound represented by general formula (I) or the compound represented by general formula (III) and the acid catalyst are the same acid.

[6] The method according to any one of [1] to [5], wherein in general formula (I):

the substituent is at least one group selected from the group consisting of monovalent aliphatic hydrocarbon groups of at least 1 but not more than 10 carbon atoms, monovalent aromatic cyclic groups of at least 6 but not more than 10 carbon atoms, groups represented by general formula (II-1) shown above, and groups represented by general formula (II-2) shown above, $R^{12}$ is a group represented by general formula (II-1) shown above or a group represented by general formula (II-2) shown above, $R^{13}$ is a hydrogen atom, and n11 is 1; and in general formula (III):

the substituent is at least one group selected from the group consisting of monovalent aliphatic hydrocarbon groups of at least 1 but not more than 10 carbon atoms, monovalent aromatic cyclic groups of at least 6 but not more than 10 carbon atoms, groups represented by general formula (II-1) shown above, groups represented by general formula (II-2) shown above, groups represented by general formula (II-3) shown above, and groups represented by general formula (II-4) shown above, and $R^{32}$ is at least one group selected from the group consisting of groups represented by general formula (II-1) shown above, groups represented by general formula (II-2) shown above, and groups represented by general formula (II-3) shown above.

[7] The method according to any one of [1] to [6], wherein the compound represented by general formula (I) or the compound represented by general formula (III), or a salt thereof, is reacted with the compound represented by general formula (IV-I) or an inorganic acid salt thereof.

[8] The method according to [7], wherein in general formula (I):

$R^{11}$ represents a hydrogen atom or a monovalent aliphatic hydrocarbon group of at least 1 but not more than 10 carbon atoms which may have a substituent, the substituent is a group represented by general formula (II-1) shown above, $R^{12}$ is a group represented by general formula (II-1) shown above, and $R^{13}$ is a hydrogen atom; and in general formula (IV-1):

$Y^{401}$ is a divalent aliphatic hydrocarbon group of at least 1 but not more than 10 carbon atoms, and $R^{401}$ is a group represented by general formula (II-1) shown above.

[9] The method according to any one of [2] to [8], wherein the acid catalyst is included in an amount of 1 ppm to 5% by mass.

Effects of the Invention

By using the production method of the aspects described above, an amino acid aminoalkyl ester or an inorganic acid salt thereof can be produced in high yield without acid distillation.

EMBODIMENTS FOR CARRYING OUT THE INVENTION

<<Method for Producing Amino Acid Aminoalkyl Ester or Inorganic Acid Salt Thereof>>

The production method of this embodiment of the present invention is a method for producing an amino acid aminoalkyl ester or an inorganic acid salt thereof by reacting a compound represented by general formula (I) shown below (hereafter sometimes referred to as "the compound (I)") or a compound represented by general formula (III) shown below (hereafter sometimes referred to as "the compound (III)"), or a salt thereof, and at least one compound selected from the group consisting of compounds represented by general formula (IV-I) shown below (hereafter sometimes referred to as "the compound (IV-I)"), compounds represented by general formula (IV-II) shown below (hereafter sometimes referred to as "the compound (IV-II)"), compounds represented by general formula (IV-III) shown below (hereafter sometimes referred to as "the compound (IV-III)"), and compounds represented by general formula (IV-IV) shown below (hereafter sometimes referred to as "the compound (IV-IV)"), or an inorganic acid salt thereof. Further, in the production method of the present embodiment, the reaction may be conducted in the presence of an acid catalyst having a normal boiling point of 0° C. or higher. The acid catalyst may be an organic acid or an inorganic acid.

[Chemical formula 8]

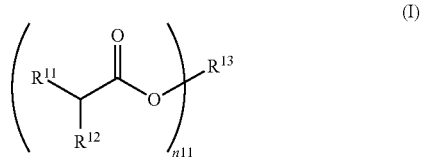

(In general formula (I), $R^{11}$ represents a hydrogen atom, a monovalent aliphatic hydrocarbon group of at least 1 but not more than 10 carbon atoms which may have a substituent, or a monovalent aromatic cyclic group of at least 6 but not more than 10 carbon atoms which may have a substituent. The substituent is at least one group selected from the group consisting of monovalent aliphatic hydrocarbon groups of at least 1 but not more than 10 carbon atoms, monovalent aromatic cyclic groups of at least 6 but not more than 10 carbon atoms, halogeno groups, alkoxy groups, thioalkyl groups, a primary amino group (—$NH_2$), a carboxyl group, a carbamide group (—$NHCONH_2$), groups represented by general formula (II-1) shown below (hereafter sometimes referred to as "the group (I-1)"), groups represented by general formula (II-2) shown below (hereafter sometimes referred to as "the group (II-2)"), groups represented by general formula (II-3) shown below (hereafter sometimes referred to as "the group (II-3)"), and groups represented by general formula (II-4) shown below (hereafter sometimes referred to as "the group (II-4)"). $R^{12}$ represents an amino group, a carbamide group (—$NHCONH_2$), a group represented by general formula (II-1) shown below, a group represented by general formula (II-2) shown below, or a group represented by general formula (II-3) shown below. $R^{13}$ represents a hydrogen atom or an n11-valent organic group. Further, n11 is an integer of at least 1 but not more than 4.)

[Chemical formula 9]

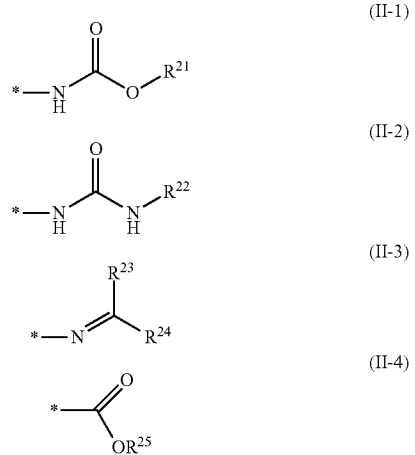

(In general formula (II-1), $R^{21}$ represents a monovalent aliphatic hydrocarbon group of at least 1 but not more than 10 carbon atoms which may have a substituent, or a monovalent aromatic cyclic group of at least 6 but not more than 10 carbon atoms which may have a substituent.

In general formula (II-2), $R^{22}$ represents a monovalent organic group.

In general formula (II-3), each of $R^{23}$ and $R^{24}$ independently represents a monovalent aliphatic hydrocarbon group of at least 1 but not more than 10 carbon atoms which may have a substituent, or a monovalent aromatic cyclic group of at least 6 but not more than 10 carbon atoms which may have a substituent.

In general formula (II-4), $R^{25}$ represents a hydrogen atom or a monovalent organic group.

[Chemical formula 10]

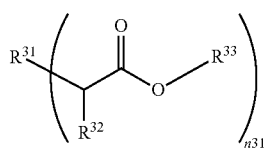

(In general formula (III), n31 is an integer of at least 2 but not more than 4. $R^3$ represents an n31-valent aliphatic hydrocarbon group of at least 1 but not more than 10 carbon atoms which may have a substituent, or an n31-valent aromatic cyclic group of at least 6 but not more than 10 carbon atoms which may have a substituent. The substituent is at least one group selected from the group consisting of monovalent aliphatic hydrocarbon groups of at least 1 but not more than 10 carbon atoms, monovalent aromatic cyclic groups of at least 6 but not more than 10 carbon atoms, halogeno groups, alkoxy groups, thioalkyl groups, a primary amino group (—$NH_2$), a carboxyl group, a carbamide group (—$NHCONH_2$), groups represented by general formula (II-1) shown above, groups represented by general formula (II-2) shown above, groups represented by general formula (II-3) shown above, and groups represented by general formula (II-4) shown above. $R^{32}$ represents an amino group, a carbamide group (—$NHCONH_2$), a group represented by general formula (II-1) shown above, a group represented by general formula (II-2) shown above, or a group represented by general formula (II-3) shown above. $R^{33}$ represents a hydrogen atom or a monovalent organic group.)

[Chemical formula 11]

(In general formula (IV-1), $Y^{401}$ represents a divalent aliphatic hydrocarbon group of at least 1 but not more than 10 carbon atoms or a divalent aromatic cyclic group of at least 6 but not more than 10 carbon atoms. $R^{401}$ represents an amino group, a carbamide group (—$NHCONH_2$), a group represented by general formula (II-1) shown above, a group represented by general formula (II-2) shown above, or a group represented by general formula (II-3) shown above.)

[Chemical formula 12]

(In general formula (IV-II), each of $Y^{402}$ and $Y^{403}$ independently represents a divalent aliphatic hydrocarbon group of at least 1 but not more than 10 carbon atoms or a divalent aromatic cyclic group of at least 6 but not more than 10 carbon atoms. Each of $R^{402}$ and $R^{403}$ independently represents at least one group selected from the group consisting of a hydrogen, an amino group, a carbamide group (—$NHCONH_2$), groups represented by general formula (II-1) shown above, groups represented by general formula (II-2) shown above, groups represented by general formula (II-3) shown above, and groups represented by general formula (II-4) shown above.)

[Chemical formula 13]

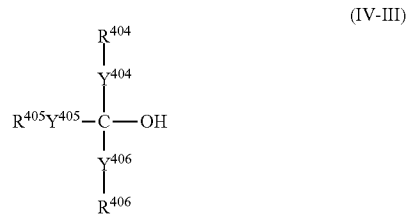

(IV-III)

(In general formula (V-Ill), each of $Y^{404}$, $Y^{405}$ and $Y^{406}$ independently represents a divalent aliphatic hydrocarbon group of at least 1 but not more than 10 carbon atoms or a divalent aromatic cyclic group of at least 6 but not more than 10 carbon atoms. Each of $R^{404}$, $R^{405}$ and $R^{406}$ independently represents at least one group selected from the group consisting of a hydrogen, an amino group, a carbamide group (—$NHCONH_2$), groups represented by general formula (II-1) shown above, groups represented by general formula (II-2) shown above, groups represented by general formula (II-3) shown above, and groups represented by general formula (II-4) shown above.)

[Chemical formula 14]

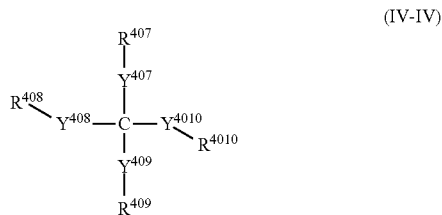

(IV-IV)

(In general formula (IV-IV), each of $Y^{407}$, $Y^{408}$, $Y^{409}$ and $Y^{4010}$ represents a divalent aliphatic hydrocarbon group of at least 1 but not more than 10 carbon atoms or a divalent aromatic cyclic group of at least 6 but not more than 10 carbon atoms. At least one of $R^{407}$, $R^{408}$, $R^{409}$ and $R^{4010}$ represents a hydroxyl group, and each of the others represents at least one group selected from the group consisting of a hydrogen, an amino group, a carbamide group (—$NHCONH_2$), groups represented by general formula (II-1) shown above, groups represented by general formula (II-2) shown above, groups represented by general formula (II-3) shown above, and groups represented by general formula (II-4) shown above.)

By using the production method of the present embodiment, an amino acid aminoalkyl ester or an inorganic acid salt thereof can be produced in high yield without acid distillation.

The compound (I) and the compound (III) used in the production method of the present embodiment are compounds which have an α-amino acid skeleton. In an α-amino acid, there are two possible three-dimensional bonding arrangements of the amino group and the carboxyl group and the like to the α-carbon atom, and these arrangements are distinguished as the D- and L-optical isomers.

The α-amino acid (or the compound having an amino acid skeleton) used in the production method of the present embodiment may be the D-isomer, the L-isomer, or a mixture thereof. Most amino acids that can be obtained industrially at low cost are amino acids produced by fermentation, and are almost all L-isomers, and these amino acids can be used favorably. In this description, the three-dimensional configuration is not shown, indicating that either the D-isomer or the L-isomer may be used.

<Reaction Conditions>

In the production method of the present embodiment, an amino acid aminoalkyl ester or an inorganic acid salt thereof is produced by subjecting the compound (I) or the compound (III) or a salt thereof, and at least one compound selected from the group consisting of the compound (IV-I), the compound (IV-II), the compound (IV-III) and the compound (IV-IV), or a salt thereof, to an esterification reaction or a transesterification reaction. Because this reaction is a dehydration reaction, water is produced as a by-product. By removing this water from the reaction system, the amino acid aminoalkyl ester or inorganic acid salt thereof can be produced efficiently. At this time, a carrying agent such as an inert gas or an organic solvent that undergoes azeotropic distillation with water may be used to remove the water from the reaction system. This reaction may be conducted in the presence of an acid catalyst having a normal boiling point of 0° C. or higher.

Furthermore, in those cases where a salt of the compound (I) or a salt of the compound (III) is used as a raw material, the type of acid used for forming the salt with the compound (I) or the compound (III) and the type of acid used as a catalyst may be the same or different. Among the various possibilities, from the viewpoints of the production costs and simplifying the production of the reaction product, the type of acid used for forming the salt with the compound (I) or the compound (III) and the type of acid used as a catalyst are preferably the same.

Although there are no particular limitations on the blend ratio (molar ratio) between the compound (I) or the compound (III) or the salt thereof, and the at least one compound selected from the group consisting of the compound (IV-I), the compound (IV-II), the compound (IV-I) and the compound (IV-IV), or the salt thereof, the molar ratio between the ester group of the compound (I) or the compound (III) or a salt thereof, and the hydroxyl group of the at least one compound selected from the group consisting of the compound (IV-I), the compound (IV-II), the compound (IV-Ill) and the compound (IV-IV), or the salt thereof, is preferably from 1:0.5 to 1:5, and is more preferably from 1:1 to 1:3.

The reaction temperature is preferably at least 30° C. but not more than 200° C., more preferably at least 50° C. but not more than 180° C., and even more preferably at least 70° C. but not more than 150° C.

The pressure is preferably at least 1 kPa but not more than 150 kPa, more preferably at least 5 kPa but not more than 100 kPa, and even more preferably at least 10 kPa but not more than 80 kPa.

In those cases where an acid catalyst is used, the amount used of the catalyst, relative to the total mass of the reaction liquid, is preferably at least 3% by mass but not more than 80% by mass, more preferably at least 5% by mass but not more than 70% by mass, and even more preferably at least 6% by mass but not more than 60% by mass.

The reaction time is not particularly limited, but is preferably at least 0.01 hours but not longer than 100 hours, more preferably at least 3 hours but not longer than 15 hours, and even more preferably at least 5 hours but not longer than 10 hours. Further, the reaction time may also be determined on the basis of the amount produced of the target product. For example, the reaction liquid may be sampled and the amount of the target product quantified, with the reaction stopped when a predetermined yield has been reached.

An aqueous solution of an inorganic acid may be added to the reaction system. There are no particular limitations on the amount used of the inorganic acid aqueous solution, but a molar amount of at least 1.0 times but not more than 5.0 times the total molar amount of the compound (I) or the compound (III) or the salt thereof, and the at least one compound selected from the group consisting of the compound (IV-I), the compound (IV-II), the compound (IV-II) and the compound (IV-IV), or the salt thereof is preferred. The concentration of the inorganic acid aqueous solution is preferably at least 20% by mass but not more than 35% by mass.

Further, the obtained amino acid aminoalkyl ester or the inorganic acid salt thereof may be an inorganic acid salt having from 1 to a plurality of moles of the inorganic acid per 1 mol of the amino acid aminoalkyl ester.

Furthermore, in those cases where the obtained amino acid aminoalkyl ester is not a salt of the desired inorganic acid, the desired inorganic acid salt may be formed by performing a salt exchange or the like.

Production of the target product can be confirmed by analysis of the reaction liquid using a conventional method such as liquid chromatography.

Further, the amino acid aminoalkyl ester or the inorganic acid salt thereof may be extracted from the reaction liquid, and purified using a conventional purification method such as crystallization or column chromatography.

Furthermore, the amino acid aminoalkyl ester or the inorganic acid salt thereof obtained using the production method of the present embodiment may be used to produce a compound having an isocyanate group by conducting a carbamation using a conventional method, and then subjecting the carbamate to thermal decomposition.

<Raw Materials and Products>

The raw materials used in the production method of the present embodiment and the resulting products are described below in further detail.

[Compound (I)]

The compound (I) is a compound represented by general formula (I) shown below, and is an amino acid or an amino acid ester, or a derivative thereof.

Further, the compound (I) may exist in the form of a salt with an acid. The acid that forms the salt with the compound (I) may be an organic acid or an inorganic acid. Examples of these types of acids include the same acids as those exemplified below in relation to the "acid catalyst". Among the various possibilities, the acid that forms a salt with the compound (I) is preferably an inorganic acid. Further, hydrochloric acid may be used as the acid that forms a salt with the compound (I).

[Chemical formula 15]

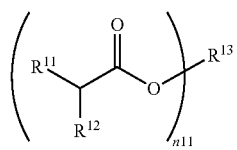

(I)

($R^{11}$)

In general formula (I), $R^{11}$ represents a hydrogen atom, a monovalent aliphatic hydrocarbon group of at least 1 but not more than 10 carbon atoms which may have a substituent, or a monovalent aromatic cyclic group of at least 6 but not more than 10 carbon atoms which may have a substituent.

The aliphatic hydrocarbon group of at least 1 but not more than 10 carbon atoms for $R^{11}$ may be linear, branched or cyclic, but is preferably linear or branched.

Examples of linear aliphatic hydrocarbon groups include a methyl group, ethyl group, n-propyl group, n-butyl group, n-pentyl group, n-hexyl group, n-heptyl group, n-octyl group, n-nonyl group and n-decyl group.

Examples of branched aliphatic hydrocarbon groups include an isopropyl group, isobutyl group, sec-butyl group, tert-butyl group, isopentyl group, sec-pentyl group, neopentyl group, tert-pentyl group, 2,3-dimethylpropyl group, 1-ethylpropyl group, 1-methylbutyl group, 2-methylbutyl group, isohexyl group, 2-methylpentyl group, 3-methylpentyl group, 1,1,2-trimethylpropyl group, 3,3-dimethylbutyl group and 1-methylheptyl group.

The monovalent aromatic cyclic group of at least 6 but not more than 10 carbon atoms for $R^{11}$ may be an aromatic hydrocarbon group or an aromatic heterocyclic group.

Examples of aromatic hydrocarbon groups include a phenyl group and a naphthyl group.

Examples of aromatic heterocyclic groups include a benzyloxazolyl group and a furanyl group.

The aforementioned substituent is at least one group selected from the group consisting of monovalent aliphatic hydrocarbon groups of at least 1 but not more than 10 carbon atoms, monovalent aromatic cyclic groups of at least 6 but not more than 10 carbon atoms, halogeno groups, alkoxy groups (—OR), thioalkyl groups (—SR), a primary amino group (—$NH_2$), a carboxyl group, a carbamide group (—$NHCONH_2$), groups represented by general formula (II-1) shown below (groups having a urethane linkage), groups represented by general formula (II-2) shown below (groups having a urea linkage), groups represented by general formula (II-3) shown below (tertiary amino groups), and groups represented by general formula (II-4) shown below (groups having an ester linkage).

Examples of the halogeno groups include a fluoro group, chloro group, bromo group and iodo group.

Examples of the alkoxy groups include a methoxy group, ethoxy group, propoxy group, isopropoxy group, butoxy group, sec-butoxy group, tert-butoxy group, pentyloxy group and neopentyloxy group.

Examples of the thioalkyl groups include a thioethyl group, thiomethyl group and thiopropynyl group.

[Chemical formula 16]

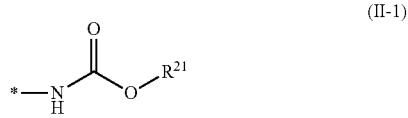

(II-1)

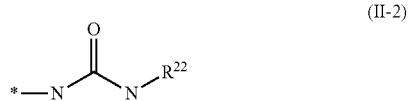

(II-2)

(II-3)

(II-4)

In general formula (II-1), $R^{21}$ represents a monovalent aliphatic hydrocarbon group of at least 1 but not more than 10 carbon atoms which may have a substituent, or a monovalent aromatic cyclic group of at least 6 but not more than 10 carbon atoms which may have a substituent.

In general formula (II-2), $R^{22}$ represents a monovalent organic group.

In general formula (II-3), each of $R^{23}$ and $R^{24}$ independently represents a monovalent aliphatic hydrocarbon group of at least 1 but not more than 10 carbon atoms which may have a substituent, or a monovalent aromatic cyclic group of at least 6 but not more than 10 carbon atoms which may have a substituent.

In general formula (II-4), $R^{25}$ represents a hydrogen atom or a monovalent organic group.

The asterisks indicate bonding sites.

Examples of the monovalent aliphatic hydrocarbon group of at least 1 but not more than 10 carbon atoms which may have a substituent and the monovalent aromatic cyclic group of at least 6 but not more than 10 carbon atoms which may have a substituent for $R^{21}$, $R^{23}$ and $R^{24}$ include the same groups as those exemplified above for $R^{11}$. Further, the substituent in $R^{21}$, $R^{23}$ and $R^{24}$ is preferably an aliphatic hydrocarbon group of at least 1 but not more than 5 carbon atoms or a phenyl group.

Examples of the monovalent organic group for $R^{22}$ and $R^{25}$ include an aliphatic hydrocarbon group, an aromatic hydrocarbon group, or a group in which an aliphatic hydrocarbon group and an aromatic hydrocarbon group are bonded together. Specific examples of $R^{22}$ and $R^{25}$ include cyclic hydrocarbon groups, acyclic hydrocarbon groups, and groups in which an acyclic hydrocarbon group and at least one cyclic group are bonded together. Examples of the cyclic group include cyclic hydrocarbon groups, heterocyclic groups, heterocyclic spiro groups, and hetero-crosslinked cyclic groups. Examples of the cyclic hydrocarbon groups include monocyclic hydrocarbon groups, condensed polycyclic hydrocarbon groups, crosslinked cyclic hydrocarbon groups, spiro hydrocarbon groups, ring-aggregated hydrocarbon groups, and cyclic hydrocarbon groups having a side chain.

Among the various possibilities, $R^{22}$ is preferably a group in which one amino group has been removed from an amino acid or an amino acid ester, and groups represented by general formula (I) shown below (hereafter sometimes referred to as "group (1)") are preferred.

[Chemical formula 17]

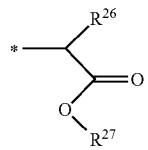

(1)

In general formula (I), $R^{26}$ is the same as $R^{22}$ described above. Accordingly, in those cases when $R^{26}$ includes the above group (1), $R^{22}$ is a group in which a plurality of the above groups (1) are linked together, either directly or via a divalent linking group.

Further, $R^{27}$ represents a hydrogen atom or a monovalent organic group. Examples of the monovalent organic group for $R^{27}$ include the same groups as those exemplified above for $R^{22}$ and $R^{25}$. Among the various possibilities, $R^{27}$ is preferably a hydrogen atom, a monovalent aliphatic hydrocarbon group of at least 1 but not more than 10 carbon atoms, or a monovalent aromatic hydrocarbon group of at least 6 but not more than 10 carbon atoms, and is more preferably a hydrogen atom or a monovalent aliphatic hydrocarbon group of at least 1 but not more than 5 carbon atoms.

Among the various possibilities, $R^{11}$ is preferably a hydrogen atom, a hydrocarbon group of at least 1 but not more than 3 carbon atoms having a substituent, an unsubstituted linear aliphatic hydrocarbon group of at least 1 but not more than 10 carbon atoms, a phenyl group which may have a substituent, an unsubstituted naphthyl group, or an unsubstituted aromatic heterocyclic group.

($R^{12}$)

$R^{12}$ represents an amino group, a carbamide group (—$NHCONH_2$), the group (II-1) described above, the group (II-2) described above, or the group (II-3) described above, and is preferably the group (II-1).

(n11)

Further, n11 is an integer of at least 1 but not more than 4, and is preferably an integer of at least 1 but not more than 3, more preferably 1 or 2, and even more preferably 1.

($R^{13}$)

$R^{13}$ represents a hydrogen atom or an n11-valent organic group.

Examples of the organic group for R include the same groups as those exemplified above for $R^{22}$ and $R^{25}$.

When $R^{13}$ is monovalent, a hydrogen atom, a monovalent aliphatic hydrocarbon group of at least 1 but not more than 10 carbon atoms, or an aromatic hydrocarbon group of at least 6 but not more than 10 carbon atoms is preferred, and a hydrogen atom or a monovalent aliphatic hydrocarbon group of at least 1 but not more than 5 carbon atoms is more preferred.

When $R^{13}$ is divalent, a divalent aliphatic hydrocarbon group of at least 1 but not more than 10 carbon atoms or a divalent aromatic hydrocarbon group of at least 6 but not more than 10 carbon atoms is preferred, and a divalent aliphatic hydrocarbon group of at least 1 but not more than 5 carbon atoms is more preferred.

Examples of the divalent aliphatic hydrocarbon groups of at least 1 but not more than 10 carbon atoms for $R^{13}$ include a methylene group, ethylene group, trimethylene group, tetramethylene group, pentamethylene group and hexamethylene group. Examples of the divalent aromatic hydrocarbon groups of at least 6 but not more than 10 carbon atoms for $R^{13}$ include a phenylene group and a naphthalenediyl group.

When $R^{13}$ is trivalent, a trivalent aliphatic hydrocarbon group of at least 1 but not more than 10 carbon atoms or a trivalent aromatic hydrocarbon group of at least 6 but not more than 10 carbon atoms is preferred, and a trivalent aliphatic hydrocarbon group of at least 1 but not more than 5 carbon atoms is more preferred.

Examples of the trivalent aliphatic hydrocarbon group of at least 1 but not more than 10 carbon atoms for $R^{13}$ include a methanetriyl group, ethanetriyl group and propanetriyl group. Examples of the trivalent aromatic hydrocarbon group of at least 6 but not more than 10 carbon atoms for $R^{13}$ include a benzenetriyl group and a naphthalenetriyl group.

When $R^{13}$ is tetravalent, a tetravalent aliphatic hydrocarbon group of at least 1 but not more than 10 carbon atoms or a tetravalent aromatic hydrocarbon group of at least 6 but not more than 10 carbon atoms is preferred, and a tetravalent aliphatic hydrocarbon group of at least 1 but not more than 5 carbon atoms is more preferred.

Examples of the tetravalent aliphatic hydrocarbon group of at least 1 but not more than 10 carbon atoms for $R^{13}$ include a methanetetrayl group, ethanetetrayl group, propanetetrayl group, butanetetrayl group, pentanetetrayl group, hexanetetrayl group, heptanetetrayl group and octanetetrayl group. Examples of the tetravalent aromatic hydrocarbon group of at least 6 but not more than 10 carbon atoms for $R^{13}$ include a benzenetetrayl group and a naphthalenetetrayl group.

Examples of preferred compounds for the compound (I) include compounds represented by general formula (I-1) shown below (hereafter sometimes referred to as "the compound (I-1)"), compounds represented by general formula (I-2) shown below (hereafter sometimes referred to as "the compound (I-2)"), compounds represented by general formula (I-3) shown below (hereafter sometimes referred to as "the compound (I-3)"), compounds represented by general formula (I-4) shown below (hereafter sometimes referred to as "the compound (I-4)"), and compounds represented by general formula (I-5) shown below (hereafter sometimes referred to as "the compound (I-5)"). Among these, the compound (I-2) is particularly preferred.

[Chemical formula 18]

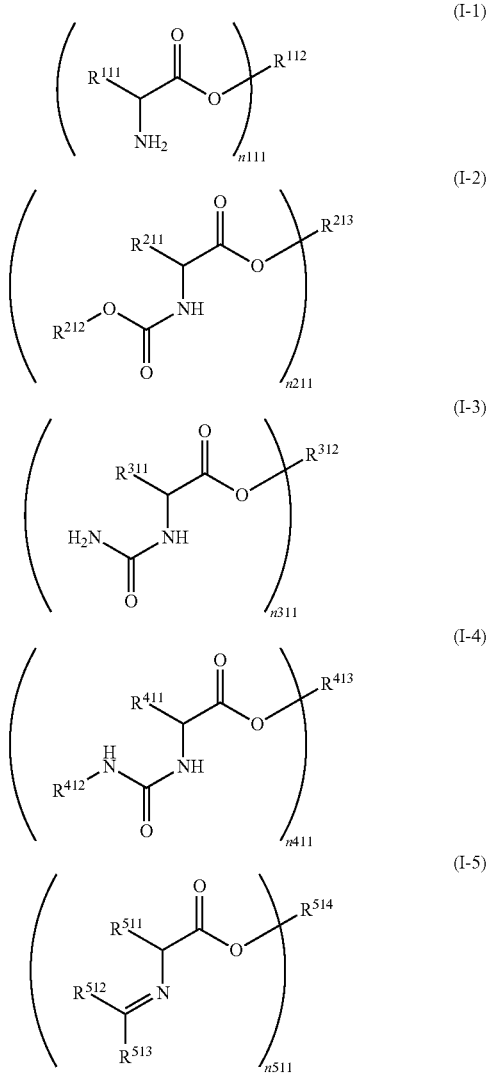

In general formula (I-1), $R^{111}$ is the same as $R^{11}$ described above. $R^{112}$ is the same as $R^{13}$ described above. Further, n111 is the same as n11 described above.

In general formula (I-2), $R^{211}$ is the same as $R^{11}$ described above. $R^{212}$ is the same as $R^{21}$ described above. $R^{213}$ is the same as $R^{13}$ described above. Further, n211 is the same as n11 described above.

In general formula (I-3), $R^{311}$ is the same as $R^{11}$ described above. $R^{312}$ is the same as $R^{13}$ described above. Further, n311 is the same as n11 described above.

In general formula (I-4), $R^{411}$ is the same as $R^{11}$ described above. $R^{412}$ is the same as $R^{22}$ described above. $R^{413}$ is the same as $R^{13}$ described above. Further, n411 is the same as n11 described above.

In general formula (I-5), $R^{511}$ is the same as $R^{11}$ described above. $R^{512}$ and $R^{513}$ are the same as $R^{23}$ described above and $R^{24}$ described above respectively. $R^{514}$ is the same as $R^{13}$ described above. Further, n511 is the same as n11 described above.

Preferred examples of the compound (I-1) include compounds represented by general formula (I-1-1) shown below (hereafter sometimes referred to as "the compound (I-1-1)"), and compounds represented by general formula (I-1-2) shown below (hereafter sometimes referred to as "the compound (I-1-2)").

[Chemical formula 19]

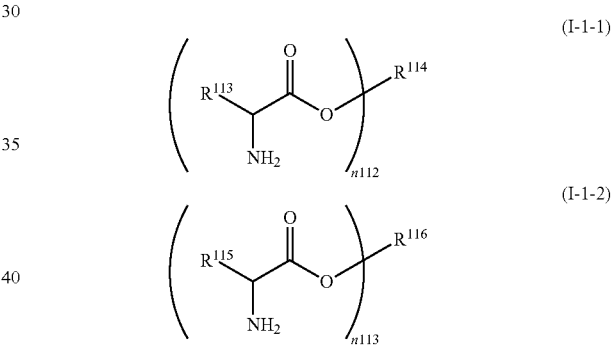

In general formula (I-1-1), $R^{113}$ represents a hydrogen atom or a monovalent aliphatic hydrocarbon group of at least 1 but not more than 10 carbon atoms which may have a substituent. Examples of the monovalent aliphatic hydrocarbon group of at least 1 but not more than 10 carbon atoms which may have a substituent for $R^{113}$ include the same groups as those exemplified above for $R^{11}$. $R^{114}$ is the same as $R^{13}$ described above. Further, n112 is the same as n11 described above.

In general formula (I-1-2), $R^{115}$ represents a monovalent aromatic cyclic group of at least 6 but not more than 10 carbon atoms which may have a substituent. Examples of the monovalent aromatic cyclic group of at least 6 but not more than 10 carbon atoms which may have a substituent for $R^{115}$ include the same groups as those exemplified above for $R^{11}$. $R^{116}$ is the same as $R^{13}$ described above. Further, n113 is the same as n11 described above.

Preferred examples of the compound (I-2) include compounds represented by general formula (I-2-1) shown below (hereafter sometimes referred to as "the compound (I-2-1)"), and compounds represented by general formula (I-2-2) shown below (hereafter sometimes referred to as "the compound (I-2-2)").

[Chemical formula 20]

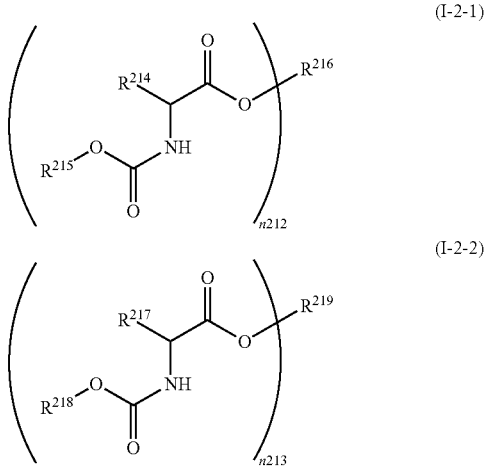

In general formula (I-2-1), $R^{214}$ is the same as $R^{113}$ described above. $R^{215}$ is the same as $R^{212}$ described above. $R^{216}$ is the same as $R^{13}$ described above. Further, n212 is the same as n11 described above.

In general formula (I-2-2), $R^{217}$ is the same as $R^{115}$ described above. $R^{218}$ is the same as $R^{212}$ described above. $R^{219}$ is the same as $R^{13}$ described above. Further, n213 is the same as n11 described above.

Preferred examples of the compound (I-3) include compounds represented by general formula (I-3-1) shown below (hereafter sometimes referred to as "the compound (I-3-1)"), and compounds represented by general formula (I-3-2) shown below (hereafter sometimes referred to as "the compound (I-3-2)").

[Chemical formula 21]

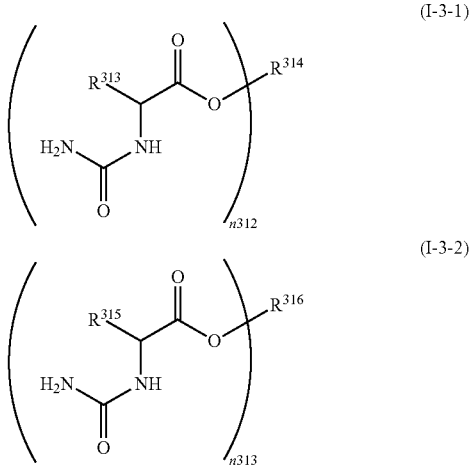

In general formula (I-3-1), $R^{313}$ is the same as $R^{113}$ described above. $R^{314}$ is the same as $R^{13}$ described above. Further, n312 is the same as n11 described above.

In general formula (I-3-2), $R^{315}$ is the same as $R^{115}$ described above. $R^{316}$ is the same as $R^{13}$ described above. Further, n313 is the same as n11 described above.

Preferred examples of the compound (I-4) include compounds represented by general formula (I-4-1) shown below (hereafter sometimes referred to as "the compound (I-4-1)"), and compounds represented by general formula (I-4-2) shown below (hereafter sometimes referred to as "the compound (I-4-2)").

[Chemical formula 22]

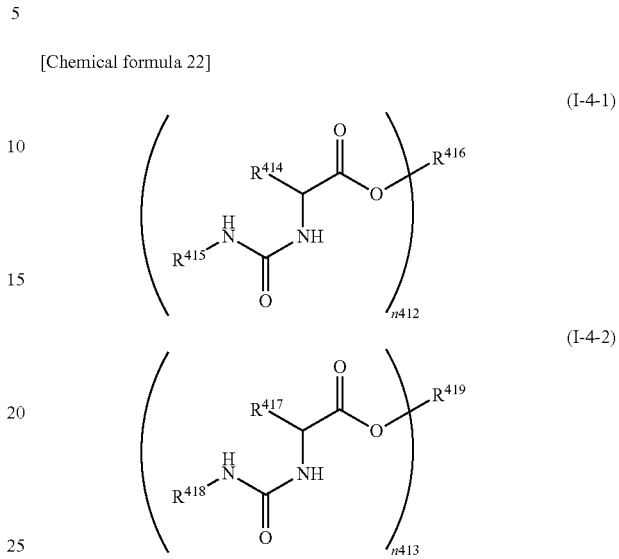

In general formula (I-4-1), $R^{414}$ is the same as $R^{113}$ described above. $R^{415}$ is the same as $R^{412}$ described above. $R^{416}$ is the same as $R^{13}$ described above. Further, n412 is the same as n11 described above.

In general formula (I-4-2), $R^{417}$ is the same as $R^{115}$ described above. $R^{418}$ is the same as $R^{412}$ described above. $R^{419}$ is the same as $R^{13}$ described above. Further, n413 is the same as n11 described above.

Preferred examples of the compound (I-5) include compounds represented by general formula (I-5-1) shown below (hereafter sometimes referred to as "the compound (I-5-1)"), and compounds represented by general formula (I-5-2) shown below (hereafter sometimes referred to as "the compound (I-5-2)").

[Chemical formula 23]

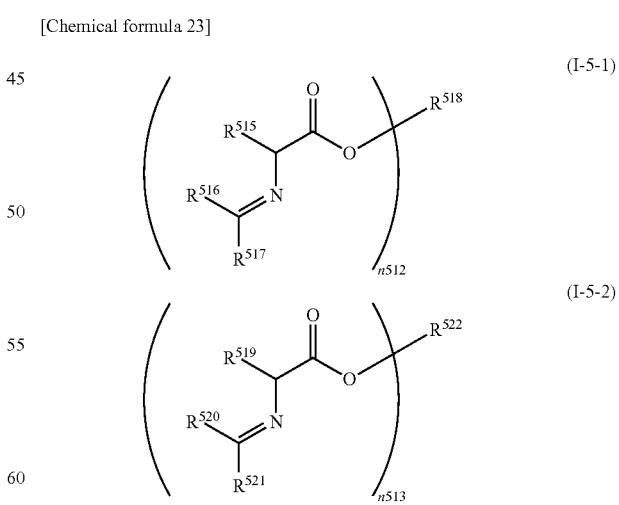

In general formula (I-5-1), $R^{515}$ is the same as $R^{13}$ described above. $R^{516}$ and $R^{517}$ are the same as $R^{512}$ described above and $R^{513}$ described above respectively. $R^{518}$ is the same as $R^{13}$ described above. Further, n512 is the same as n11 described above.

In general formula (I-5-2), $R^{19}$ is the same as $R^{15}$ described above. $R^{520}$ and $R^{521}$ are the same as $R^{512}$ described above and $R^{513}$ described above respectively. $R^{522}$ is the same as $R^{13}$ described above. Further, n513 is the same as n11 described above.

Preferred examples of the compound (I-1-1) include compounds represented by general formula (I-1-1a) shown below (hereafter sometimes referred to as "the compound (I-1-1a)"), compounds represented by general formula (I-1-1b) shown below (hereafter sometimes referred to as "the compound (I-1-1b)"), compounds represented by general formula (I-1-1c) shown below (hereafter sometimes referred to as "the compound (I-1-1c)"), compounds represented by general formula (I-1-1d) shown below (hereafter sometimes referred to as "the compound (I-1-1d)"), compounds represented by general formula (I-1-1e) shown below (hereafter sometimes referred to as "the compound (I-1-1e)"), compounds represented by general formula (I-1-1f) shown below (hereafter sometimes referred to as "the compound (I-1-1f)"), compounds represented by general formula (I-1-1g) shown below (hereafter sometimes referred to as "the compound (I-1-1g)"), compounds represented by general formula (I-1-1h) shown below (hereafter sometimes referred to as "the compound (I-1-1h)"), compounds represented by general formula (I-1-1i) shown below (hereafter sometimes referred to as "the compound (I-1-1i)"), compounds represented by general formula (I-1-1j) shown below (hereafter sometimes referred to as "the compound (I-1-1j)"), compounds represented by general formula (I-1-1k) shown below (hereafter sometimes referred to as "the compound (I-1-1k)"), and compounds represented by general formula (I-1-1m) shown below (hereafter sometimes referred to as "the compound (I-1-1m)").

[Chemical formula 24]

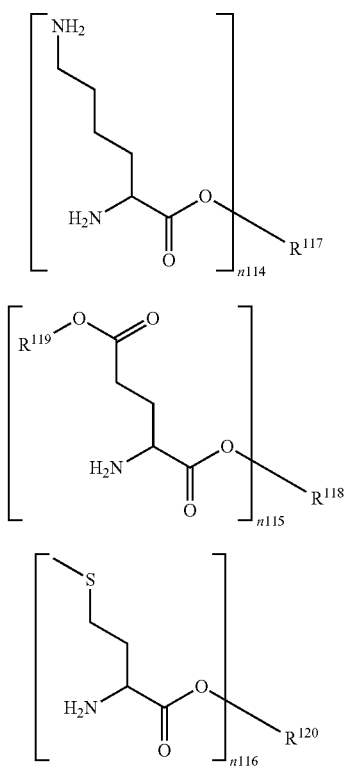

(I-1-1a)

(I-1-1b)

(I-1-1c)

[Chemical formula 25]

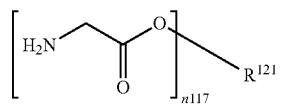

(I-1-1d)

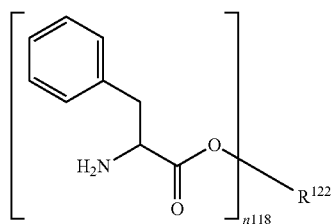

(I-1-1e)

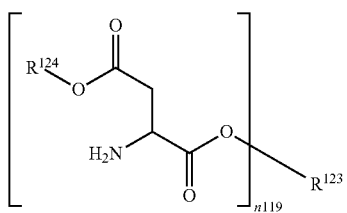

(I-1-1f)

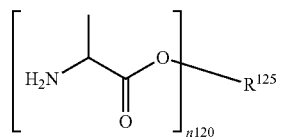

(I-1-1g)

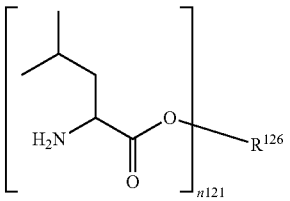

(I-1-1h)

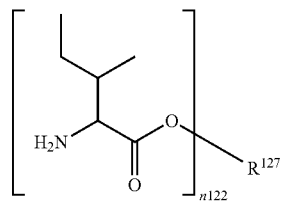

(I-1-1i)

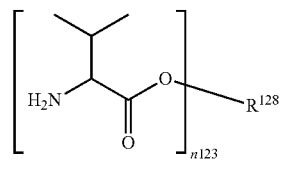

(I-1-1j)

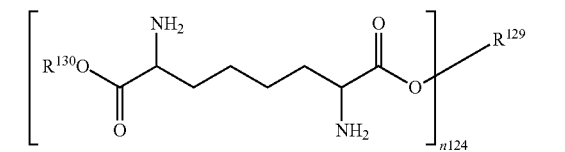

(I-1-1k)

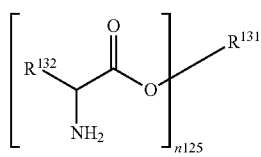

(I-1-1m)

In general formula (I-1-1a) to general formula (I-1-1m), each of $R^{117}$, $R^{118}$, $R^{120}$, $R^{121}$, $R^{122}$, $R^{123}$, $R^{125}$, $R^{126}$, $R^{27}$, $R^{128}$, $R^{129}$ and $R^{131}$ is the same as $R^{13}$ described above. Each of $R^{19}$, $R^{24}$ and $R^{130}$ independently represents a hydrogen atom, a monovalent aliphatic hydrocarbon group of at least 1 but not more than 10 carbon atoms, or a monovalent aromatic hydrocarbon group of at least 6 but not more than 10 carbon atoms. Examples of the monovalent aliphatic hydrocarbon group of at least 1 but not more than 10 carbon atoms and the monovalent aromatic hydrocarbon group of at least 6 but not more than 10 carbon atoms include the same groups as those exemplified above for $R^{11}$.

$R^{132}$ represents a linear aliphatic hydrocarbon group of at least 2 but not more than 9 carbon atoms.

Further, each of n114, n115, n116, n117, n118, n119, n120, n121, n123, n124 and n125 independently represents an integer of at least 1 but not more than 4.

For example, when n114 is 1 in the compound (I-1-1a), one example is the compound represented by formula ((I-1-1a)-1) shown below. Further, when n114 is 3, one example is the compound represented by formula ((I-1-1a)-2) shown below. Further, when n114 is 4, one example is the compound represented by formula ((I-1-1a)-3) shown below. Furthermore, when $R^{118}$, $R^{120}$, $R^{121}$, $R^{122}$, $R^{123}$, $R^{125}$, $R^{126}$, $R^{127}$, $R^{128}$, $R^{129}$ and $R^{131}$ are either trivalent or tetravalent, the compounds (I-1-1b) to (I-1-1m) can adopt similar structures to those shown below for the compound ((I-1-1a)-2) or the compound ((I-1-1a)-3).

[Chemical formula 26]

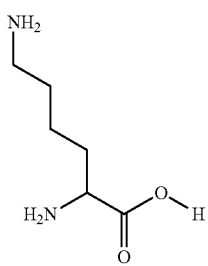

((I-1-1a)-1)

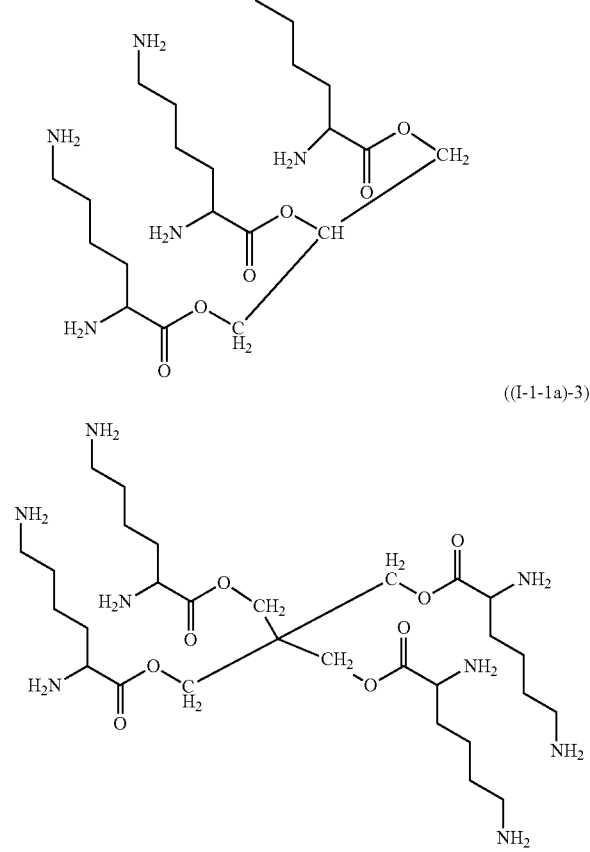

Further, in those cases where $R^{117}$, $R^{118}$, $R^{119}$, $R^{120}$, $R^{121}$, $R^{122}$, $R^{123}$, $R^{124}$, $R^{125}$, $R^{126}$, $R^{127}$ and $R^{128}$ are hydrogen atoms, the compounds (I-1-1a) to (I-1-1j) represent the amino acids listed below.

Compound (I-1-1a): lysine
Compound (I-1-1b): glutamic acid
Compound (I-1-1c): methionine
Compound (I-1-1d): glycine
Compound (I-1-1e): phenylalanine
Compound (I-1-1f): aspartic acid
Compound (I-1-1g): alanine
Compound (I-1-1h): leucine
Compound (I-1-1i): isoleucine
Compound (I-1-1j): valine Preferred examples of the compound (I-1-2) include compounds represented by general formula (I-1-2a) shown below (hereafter sometimes referred to as "the compound (I-1-2a)"), compounds represented by general formula (I-1-2b) shown below (hereafter sometimes referred to as "the compound (I-1-2b)"), compounds represented by general formula (I-1-2c) shown below (hereafter sometimes referred to as "the compound (I-1-2c)"), compounds represented by general formula (I-1-2d) shown below (hereafter sometimes referred to as "the compound (I-1-2d)"), compounds represented by general formula (I-1-2e) shown below (hereafter sometimes referred to as "the compound (I-1-2e)"), and compounds represented by general formula (I-1-2f) shown below (hereafter sometimes referred to as "the compound (I-1-2f)").

[Chemical formula 27]

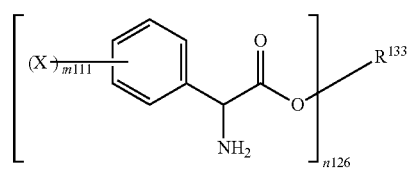
(I-1-2a)

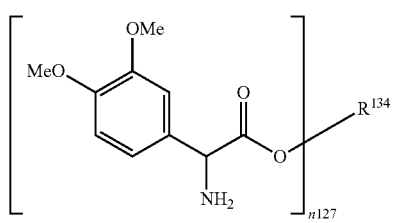
(I-1-2b)

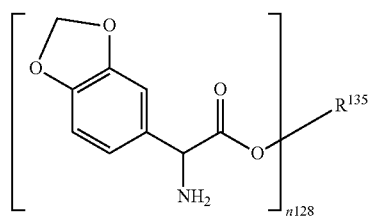
(I-1-2c)

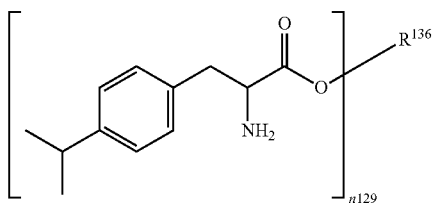
(I-1-2d)

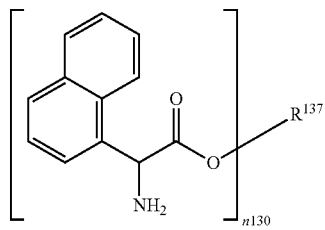
(I-1-2e)

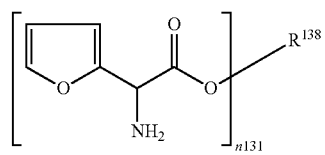
(I-1-2f)

In general formula (I-1-2a) to general formula (I-1-2f), each of $R^{133}$, $R^{134}$, $R^{135}$, $R^{136}$, $R^{137}$ and $R^{138}$ is the same as $R^{13}$ described above. Each of n126, n127, n128, n129, n130 and n131 is the same as n11 described above. Further, X represents a halogeno group. Examples of the halogeno group include the same groups as those exemplified above for $R^{11}$. Further, m111 is an integer of at least 1 but not more than 5.

Furthermore, in the compound (I-1-1k), the compound (I-1-1m), and the compounds (I-1-2a) to (I-1-2f), compounds in which $R^{129}$, $R^{121}$, $R^{133}$, $R^{134}$, $R^{135}$, $R^{136}$, $R^{137}$ and $R^{138}$ are hydrogen atoms can be produced by using the Strecker reaction to are hydrogen atoms can be produced by using the Strecker reaction to introduce a functional group of the desired structure onto a side chain of one of the amino acids described above.

Preferred examples of the compound (I-2-1) include compounds represented by general formula (I-2-1a) shown below (hereafter sometimes referred to as "the compound (I-2-1a)").

[Chemical formula 28]

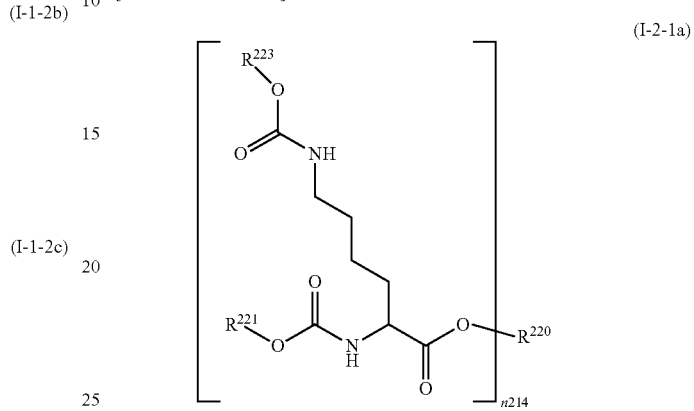
(I-2-1a)

In general formula (I-2-1a), $R^{220}$ is the same as $R^{13}$ described above. Each of $R^{221}$ and $R^{222}$ is the same as $R^{212}$ described above. Further, n214 is the same as n11 described above.

Similarly, in the compound (I-1-1b) to the compound (I-1-1m) described above, by substituting the amino group with the group (II-1) described above, structures similar to the compound (I-2-1a) or the like can be formed.

Preferred examples of the compound (I-3) include compounds represented by general formula (I-3-1a) shown below (hereafter sometimes referred to as "the compound (I-3-1a)").

[Chemical formula 29]

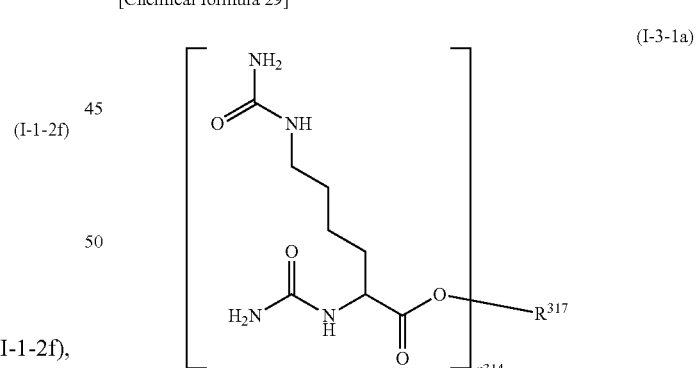
(I-3-1a)

In general formula (I-3-1a), $R^{317}$ is the same as $R^{13}$ described above. Further, n314 is the same as n11 described above.

Similarly, in the compound (I-1-1b) to the compound (I-1-1m) described above, by substituting the amino group with a carbamide group, structures similar to the compound (I-3-1a) or the like can be formed.

Preferred examples of the compound (I-4) include compounds represented by general formula (I-4-1a) shown below (hereafter sometimes referred to as "the compound (I-4-1a)").

[Chemical formula 30]

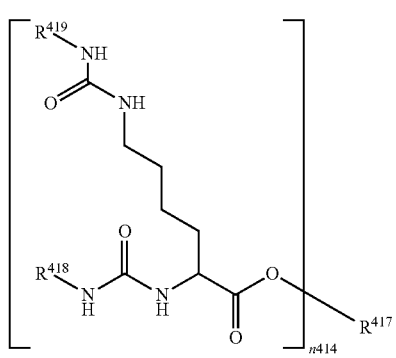

(I-4-1a)

In general formula (I-4-1a), $R^{417}$ is the same as $R^{13}$ described above. Each of $R^{418}$ and $R^{419}$ is the same as $R^{412}$ described above. Further, n414 is the same as n11 described above.

Similarly, in the compound (I-1-1b) to the compound (I-1-1m) described above, by substituting the amino group with the group (II-2) described above, structures similar to the compound (I-4-1a) or the like can be formed.

Preferred examples of the compound (I-5) include compounds represented by general formula (I-5-1a) shown below (hereafter sometimes referred to as "the compound (I-5-1a)").

[Chemical formula 31]

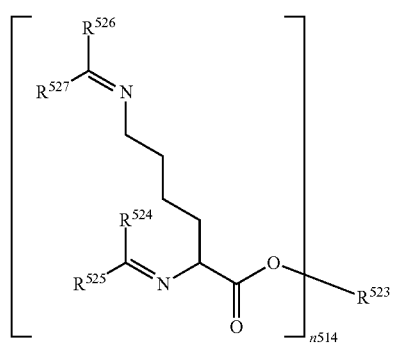

(I-5-1a)

In general formula (I-5-1a), $R^{523}$ is the same as $R^{13}$ described above. $R^{524}$, $R^{525}$, $R^{526}$ and $R^{527}$ are the same as $R^{512}$ and $R^{513}$ described above respectively. Further, n514 is the same as n11 described above.

Similarly, in the compound (I-1-1b) to the compound (I-1-1m) described above, by substituting the amino group with the group (II-3) described above, structures similar to the compound (I-5-1a) or the like can be formed.

[Compound (III)]

The compound (III) is a compound represented by general formula (III) shown below.

Further, the compound (III) may exist in the form of a salt with an acid. The acid that forms the salt with the compound (III) may be an organic acid or an inorganic acid. Examples of these types of acids include the same acids as those exemplified below in relation to the "acid catalyst". Among the various possibilities, the acid that forms a salt with the compound (III) is preferably an inorganic acid. Further, hydrochloric acid may be used as the acid that forms a salt with the compound (III).

[Chemical formula 32]

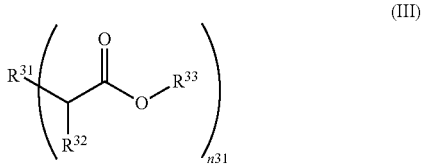

(III)

(In general formula (III), n31 is an integer of at least 2 but not more than 4. $R^{31}$ represents an n31-valent aliphatic hydrocarbon group of at least 1 but not more than 10 carbon atoms which may have a substituent, or an n31-valent aromatic cyclic group of at least 6 but not more than 10 carbon atoms which may have a substituent. The substituent is the same as the substituent described above in $R^1$. $R^{32}$ represents an amino group, a carbamide group ($—NHCONH_2$), a group represented by general formula (II-1) shown above, a group represented by general formula (II-2) shown above, or a group represented by general formula (II-3) shown above. $R^{33}$ is the same as $R^{25}$ described above.)

(n31)

Further, n31 is an integer of least 2 but not more than 4, and is preferably either 2 or 4.

($R^{31}$)

$R^{31}$ represents an n31-valent aliphatic hydrocarbon group of at least 1 but not more than 10 carbon atoms which may have a substituent, or an n31-valent aromatic cyclic group of at least 6 but not more than 10 carbon atoms which may have a substituent.

Examples of the divalent to tetravalent aliphatic hydrocarbon group of at least 1 but not more than 10 carbon atoms include the same groups as those exemplified above for $R^{13}$.

Examples of the divalent to tetravalent aromatic cyclic group of at least 6 but not more than 10 carbon atoms include the same groups as those exemplified above for $R^{13}$.

Among the various possibilities, $R^{31}$ is preferably an unsubstituted divalent or tetravalent chain-like hydrocarbon group of at least 1 but not more than 5 carbon atoms, or an unsubstituted divalent or tetravalent aromatic hydrocarbon group of at least 6 but not more than 10 carbon atoms, and is more preferably an unsubstituted divalent or tetravalent aromatic hydrocarbon group of at least 6 but not more than 10 carbon atoms.

Preferred examples of the compound (III) include compounds represented by general formula (III-1) shown below (hereafter sometimes referred to as "the compound (III-1)") and compounds represented by general formula (III-2) shown below (hereafter sometimes referred to as "the compound (III-2)").

[Chemical formula 33]

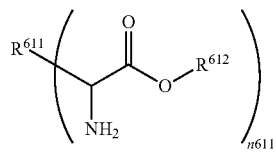

(III-1)

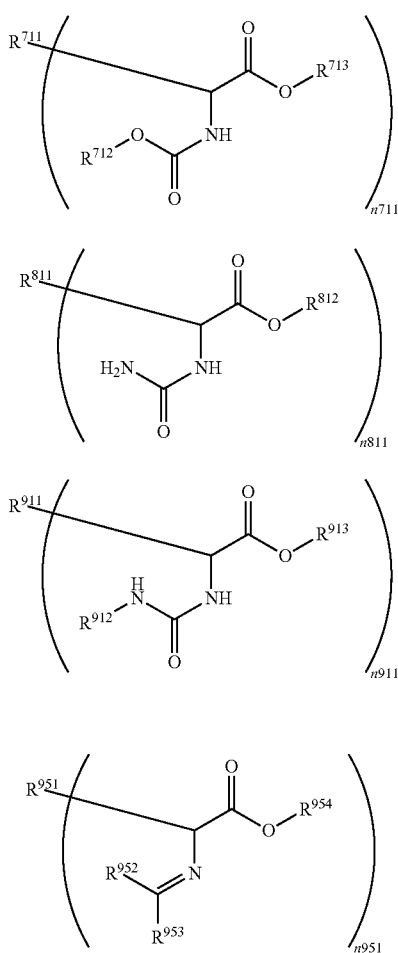

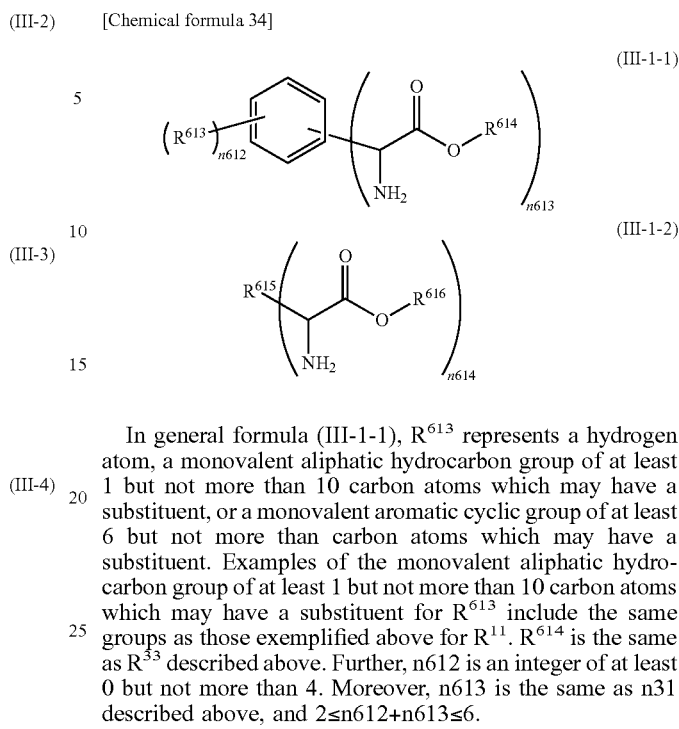

In general formula (III-1), $R^{611}$ is the same as $R^{31}$ described above. $R^{612}$ is the same as $R^{33}$ described above. Further, n611 is the same as n31 described above.

In general formula (III-2), $R^{711}$ is the same as $R^{31}$ described above. $R^{712}$ is the same as $R^{21}$ described above. $R^{713}$ is the same as $R^{33}$ described above. Further, n711 is the same as n31 described above.

In general formula (III-3), $R^{811}$ is the same as $R^{31}$ described above. $R^{812}$ is the same as $R^{33}$ described above. Further, n811 is the same as n31 described above.

In general formula (III-4), $R^{911}$ is the same as $R^{31}$ described above. $R^{912}$ is the same as $R^{22}$ described above. $R^{913}$ is the same as $R^{33}$ described above. Further, n911 is the same as n31 described above.

In general formula (III-5), $R^{951}$ is the same as $R^{31}$ described above. $R^{952}$ and $R^{953}$ are the same as $R^{23}$ described above and $R^{24}$ described above respectively. $R^{954}$ is the same as $R^{33}$ described above. Further, n911 is the same as n31 described above.

Preferred examples of the compound (III-1) include compounds represented by general formula (III-1-1) shown below (hereafter sometimes referred to as "the compound (III-1-1)"), and compounds represented by general formula (III-1-2) shown below (hereafter sometimes referred to as "the compound (III-1-2)").

[Chemical formula 34]

In general formula (III-1-1), $R^{613}$ represents a hydrogen atom, a monovalent aliphatic hydrocarbon group of at least 1 but not more than 10 carbon atoms which may have a substituent, or a monovalent aromatic cyclic group of at least 6 but not more than carbon atoms which may have a substituent. Examples of the monovalent aliphatic hydrocarbon group of at least 1 but not more than 10 carbon atoms which may have a substituent for $R^{613}$ include the same groups as those exemplified above for $R^{11}$. $R^{614}$ is the same as $R^{33}$ described above. Further, n612 is an integer of at least 0 but not more than 4. Moreover, n613 is the same as n31 described above, and 2≤n612+n613≤6.

In general formula (III-1-2), n614 is the same as n31 described above. $R^{615}$ represents an n614-valent aliphatic hydrocarbon group of at least 1 but not more than 10 carbon atoms which may have a substituent. Examples of the n614-valent aliphatic hydrocarbon group of at least 1 but not more than 10 carbon atoms which may have a substituent for $R^{615}$ include the same groups as those exemplified above for $R^{31}$. $R^{616}$ is the same as $R^{33}$ described above.

Preferred examples of the compound (III-2) include compounds represented by general formula (III-2-1) shown below (hereafter sometimes referred to as "the compound (III-2-1)"), and compounds represented by general formula (III-2-2) shown below (hereafter sometimes referred to as "the compound (III-2-2)").

[Chemical formula 35]

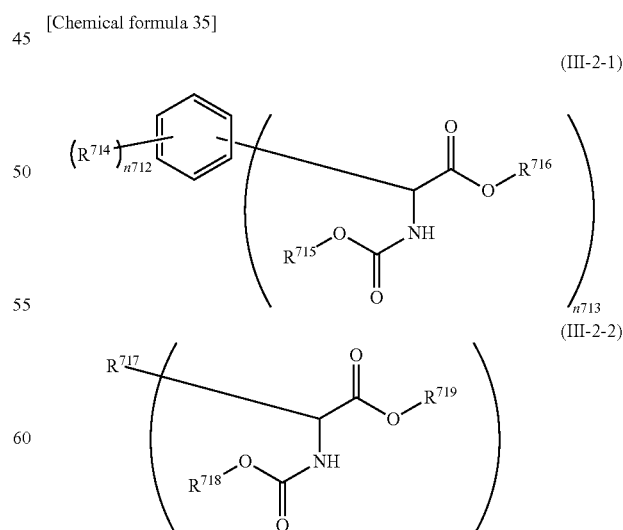

In general formula (III-2-1), $R^{714}$ is the same as $R^{613}$ described above. $R^{715}$ is the same as $R^{712}$ described above.

$R^{716}$ is the same as $R^{33}$ described above. Further, n712 is the same as n612 described above. Moreover, n713 is the same as n31 described above, and $2 \leq n712+n713 \leq 6$.

In general formula (III-2-2), $R^{717}$ is the same as $R^{615}$ described above. $R^{718}$ is the same as $R^{712}$ described above. $R^{719}$ is the same as $R^{33}$ described above. Further, n714 is the same as n31 described above.

Preferred examples of the compound (III-3) include compounds represented by general formula (III-3-1) shown below (hereafter sometimes referred to as "the compound (III-3-1)"), and compounds represented by general formula (III-3-2) shown below (hereafter sometimes referred to as "the compound (III-3-2)").

[Chemical formula 36]

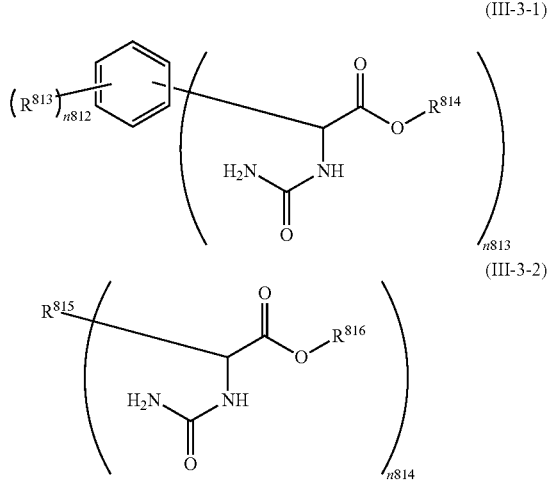

(III-3-1)

(III-3-2)

In general formula (III-3-1), $R^{813}$ is the same as $R^{613}$ described above. $R^{814}$ is the same as $R^{33}$ described above. Further, n812 is the same as n612 described above. Moreover, n813 is the same as n31 described above, and $2 \leq n812+n813 \leq 6$.

In general formula (III-3-2), $R^{815}$ is the same as $R^{615}$ described above. $R^{816}$ is the same as $R^{33}$ described above. Further, n814 is the same as n31 described above.

Preferred examples of the compound (III-4) include compounds represented by general formula (III-4-1) shown below (hereafter sometimes referred to as "the compound (III-4-1)"), and compounds represented by general formula (I-4-2) shown below (hereafter sometimes referred to as "the compound (III-4-2)").

[Chemical formula 37]

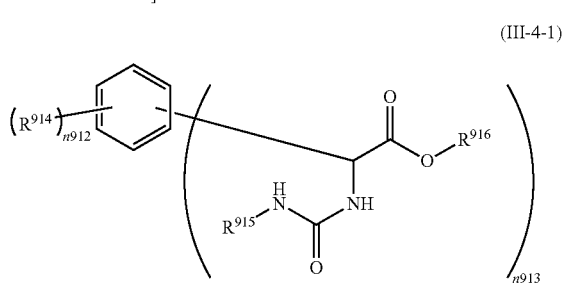

(III-4-1)

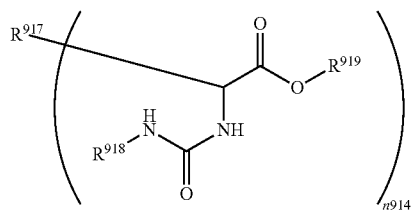

(III-4-2)

In general formula (III-4-1), $R^{914}$ is the same as $R^{613}$ described above. $R^{915}$ is the same as $R^{912}$ described above. $R^{916}$ is the same as $R^{33}$ described above. Further, n912 is the same as n612 described above. Moreover, n913 is the same as n31 described above, and $2 \leq n912+n913 \leq 6$.

In general formula (III-4-2), $R^{917}$ is the same as $R^{615}$ described above. $R^{918}$ is the same as $R^{912}$ described above. $R^{919}$ is the same as $R^{33}$ described above. Further, n914 is the same as n31 described above.

Preferred examples of the compound (III-5) include compounds represented by general formula (III-5-1) shown below (hereafter sometimes referred to as "the compound (III-5-1)"), and compounds represented by general formula (III-5-2) shown below (hereafter sometimes referred to as "the compound (III-5-2)").

[Chemical formula 38]

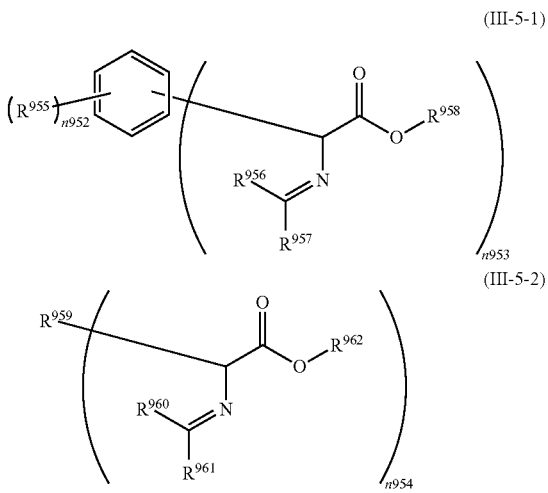

(III-5-1)

(III-5-2)

In general formula (I-5-1), $R^{955}$ is the same as $R^{613}$ described above. $R^{956}$ and $R^{957}$ are the same as $R^{912}$ described above and $R^{913}$ described above respectively. $R^{958}$ is the same as $R^{33}$ described above. Further, n952 is the same as n612 described above. Moreover, n953 is the same as n31 described above, and $2 \leq n952+n953 \leq 6$.

In general formula (I-5-2), $R^{959}$ is the same as $R^{615}$ described above. $R^{970}$ and $R^{971}$ are the same as $R^{912}$ described above and $R^{913}$ described above respectively. $R^{952}$ is the same as $R^{33}$ described above. Further, n954 is the same as n31 described above.

Preferred examples of the compound (III-1-1) include compounds represented by general formula (III-1-1a) shown below (hereafter sometimes referred to as "the compound (III-1-1a)"), and compounds represented by general formula (III-1-1b) shown below (hereafter sometimes referred to as "the compound (III-1-1b)").

[Chemical formula 39]

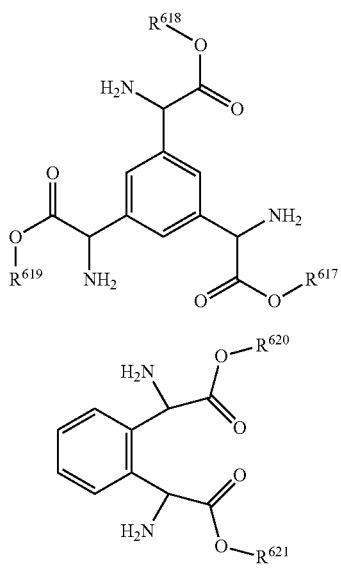

(III-1-1a)

(III-1-1b)

In general formula (III-1-1a) and general formula (III-1-1b), each of $R^{617}$, $R^{618}$, $R^{620}$ and $R^{621}$ independently represents an aliphatic hydrocarbon group of at least 1 but not more than 10 carbon atoms or an aromatic hydrocarbon group of at least 6 but not more than 10 carbon atoms. Examples of the aliphatic hydrocarbon group of at least 1 but not more than 10 carbon atoms and the aromatic hydrocarbon group of at least 6 but not more than 10 carbon atoms include the same groups as those exemplified above for $R^{11}$.

Further, in the compound (III-1-1a) and the compound (III-1-1b), by substituting each of the amino groups with the group (II-1) described above, a carbamide group, the group (II-2) described above or the group (II-3) described above, structures similar to the compound (I-2-1a), the compound (I-3-1a), the compound (I-4-1a), and the compound (I-5-1a) and the like can be formed.

[Compound (IV-I)]

The compound (IV-1) is a compound represented by general formula (IV-1) shown below.

Further, the compound (IV-I) may exist in the form of a salt with an acid. The acid that forms the salt with the compound (IV-1) may be an organic acid or an inorganic acid. Examples of these types of acids include the same acids as those exemplified below in relation to the "acid catalyst". Among the various possibilities, the acid that forms a salt with the compound (IV-1) is preferably an inorganic acid. Further, hydrochloric acid may be used as the acid that forms a salt with the compound (IV-I).

[Chemical formula 40]

(IV-1)

In general formula (IV-I), $Y^{401}$ represents a divalent aliphatic hydrocarbon group of at least 1 but not more than 10 carbon atoms or a divalent aromatic cyclic group of at least 6 but not more than 10 carbon atoms. $R^{401}$ represents an amino group, a carbamide group (—NHCONH₂), a group represented by general formula (II-1) shown above, a group represented by general formula (II-2) shown above, a group represented by general formula (II-3) shown above, or a group represented by general formula (II-4) shown above.

($Y^{401}$)

Examples of the divalent aliphatic hydrocarbon group of at least 1 but not more than 10 carbon atoms and the divalent aromatic cyclic group of at least 6 but not more than 10 carbon atoms for $Y^{401}$ include the same groups as those exemplified above in relation to $R^{13}$.

Among the various possibilities, $Y^{401}$ is preferably a divalent aliphatic hydrocarbon group of at least 1 but not more than 10 carbon atoms, more preferably a divalent aliphatic hydrocarbon group of at least 1 but not more than 5 carbon atoms, and even more preferably an ethylene group, 2'-methylethylene group, or 1',1',5-trimethylpentamethylene group.

($R^{401}$)

$R^{401}$ is preferably an amino group, a carbamide group (—NHCONH₂), a group represented by general formula (II-1) shown above, a group represented by general formula (II-2) shown above, or a group represented by general formula (II-3) shown above.

When $R^{401}$ is one of these groups, the compound (IV-1) can be represented by general formula (IV-1) to general formula (IV-5) shown below (hereafter sometimes referred to as "the compound (IV-1) to the compound (IV-5)").

[Chemical formula 41]

HO—$Y^{42}$—NH₂ (IV-1)

HO—$Y^{43}$—NHCOOR⁴² (IV-2)

HO—$Y^{44}$—NHCONH₂ (IV-3)

HO—$Y^{45}$—NHCONHR⁴³ (IV-4)

HO—$Y^{46}$—N=C(R⁴⁴)R⁴⁵ (IV-5)

In general formula (IV-1) to general formula (IV-5), each of $Y^{42}$, $Y^{43}$, $Y^{44}$, $Y^{45}$ and $Y^{46}$ independently represents a divalent aliphatic hydrocarbon group of at least 1 but not more than 5 carbon atoms. Examples of the divalent aliphatic hydrocarbon group of at least 1 but not more than 5 carbon atoms include the same groups as those exemplified above for $R^{13}$.

$R^{401}$ is the same as $R^{21}$ described above. $R^{43}$ is the same as $R^{22}$ described above. $R^{44}$ and $R^{45}$ are the same as $R^{23}$ described above and $R^{24}$ described above respectively.

Specific preferred examples of the compound (IV-1) include methanolamine, ethanolamine and propanolamine. Further, branched alkanolamines such as those shown below may also be used.

[Chemical formula 42]

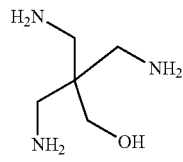

3-amino-2,2-bis(aminomethyl)-propan-1-ol

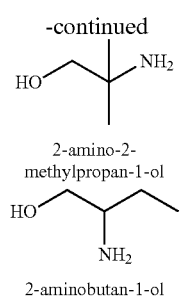

2-amino-2-methylpropan-1-ol 2-aminobutan-1-ol

Specific preferred examples of the compound (IV-2) include compounds represented by formulas (B-4) to (B-9) shown below.

[Chemical formula 43]

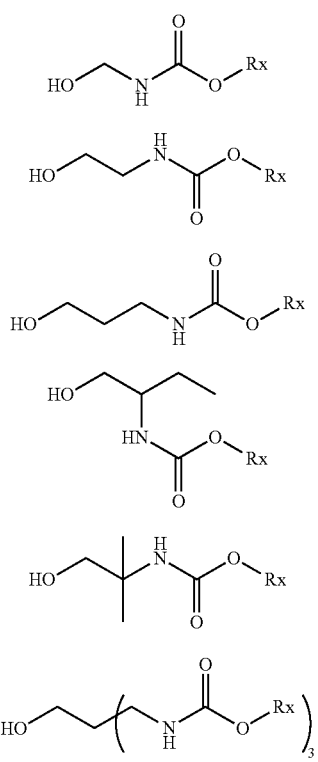

(Rx in the above formulas is preferably a methyl group, ethyl group, propyl group (including structural isomers), butyl group (including structural isomers), pentyl group (including structural isomers), hexyl group (including structural isomers), pentyl group (including structural isomers), octyl group (including structural isomers), phenyl group, methylphenyl group (including structural isomers), dimethylphenyl group (including structural isomers), ethylphenyl group (including structural isomers), and diethylphenyl group (including structural isomers)).

Specific preferred examples of the compound (IV-3) include hydroxymethyl urea and 2-hydroxyethyl urea.

Preferred examples of the compound (IV-4) include compounds represented by general formula (IV-4-1) shown below (hereafter sometimes referred to as "the compound (IV-4-1)").

[Chemical formula 44]

HO—Y$^{47}$—NHCONH—Y$^{48}$—OH    (IV-4-1)

In general formula (IV-4-1), each of Y$^{47}$ and Y$^{48}$ is the same as Y$^{42}$ described above, Y$^{43}$ described above, Y$^{44}$ described above, Y$^{45}$ described above, and Y$^{46}$ described above.

Specific preferred examples of the compound (IV-4-1) include the compound represented by formula (B-3) shown below and compounds represented by formula (B-10) shown below.

[Chemical formula 45]

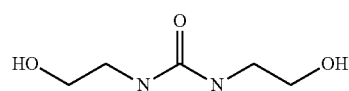

1,3-bis(2-hydroxyethyl)urea

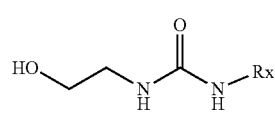

(Rx in the above formula is preferably a methyl group, ethyl group, propyl group (including structural isomers), butyl group (including structural isomers), pentyl group (including structural isomers), hexyl group (including structural isomers), pentyl group (including structural isomers), octyl group (including structural isomers), phenyl group, methylphenyl group (including structural isomers), dimethylphenyl group (including structural isomers), ethylphenyl group (including structural isomers), and diethylphenyl group (including structural isomers)).

Specific preferred examples of the compound (IV-5) include the compound represented by formula (B-11) shown below.

[Chemical formula 46]

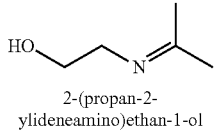

2-(propan-2-ylideneamino)ethan-1-ol

[Compound (IV-II)]

The compound (IV-II) is a compound represented by general formula (IV-II) shown below. The compound (IV-II) may exist in the form of a salt with an acid. The acid that forms the salt with the compound (IV-II) is as described above for the acid that forms a salt with the compound (IV-1),

[Chemical formula 47]

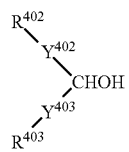

In general formula (IV-II), each of $Y^{402}$ and $Y^{403}$ independently represents a divalent aliphatic hydrocarbon group of at least 1 but not more than 10 carbon atoms or a divalent aromatic cyclic group of at least 6 but not more than 10 carbon atoms. Each of $R^{402}$ and $R^{403}$ independently represents at least one group selected from the group consisting of a hydrogen, an amino group, a carbamide group (—NHCONH$_2$), groups represented by general formula (II-1) shown above, groups represented by general formula (II-2) shown above, groups represented by general formula (II-3) shown above, and groups represented by general formula (II-4) shown above.

The divalent aliphatic hydrocarbon group of at least 1 but not more than 10 carbon atoms or the divalent aromatic cyclic group of at least 6 but not more than 10 carbon atoms for $Y^{402}$ and $Y^{403}$ is as described above for the divalent aliphatic hydrocarbon group of at least 1 but not more than 10 carbon atoms or the divalent aromatic cyclic group of at least 6 but not more than 10 carbon atoms for $Y^{401}$ in general formula (IV-I).

Specific preferred examples of the compound (IV-II) include the compounds represented by formulas (B-21) to (B-29) shown below.

[Chemical formula 48]

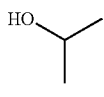
(B-21)

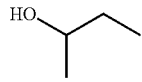
(B-22)

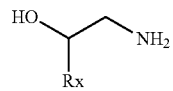
(B-23)

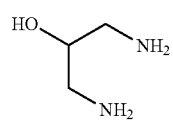
(B-24)

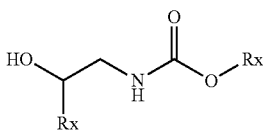
(B-25)

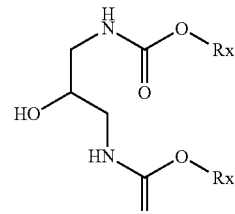
(B-26)

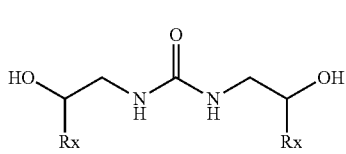
(B-27)

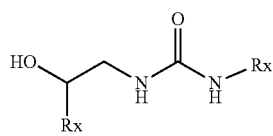
(B-28)

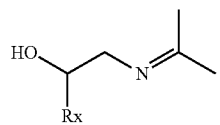
(B-29)

(Rx in the above formulas is preferably a methyl group, ethyl group, propyl group (including structural isomers), butyl group (including structural isomers), pentyl group (including structural isomers), hexyl group (including structural isomers), pentyl group (including structural isomers), octyl group (including structural isomers), phenyl group, methylphenyl group (including structural isomers), dimethylphenyl group (including structural isomers), ethylphenyl group (including structural isomers), and diethylphenyl group (including structural isomers)).

[Compound (IV-III)]

The compound (IV-III) is a compound represented by general formula (IV-III) shown below. The compound (IV-III) may exist in the form of a salt with an acid. The acid that forms the salt with the compound (IV-III) is as described above for the acid that forms a salt with the compound (IV-I),

[Chemical formula 49]

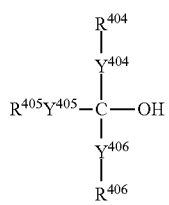
(IV-III)

In general formula (IV-III), each of $Y^{404}$, $Y^{405}$ and $Y^{406}$ independently represents a divalent aliphatic hydrocarbon group of at least 1 but not more than 10 carbon atoms or a divalent aromatic cyclic group of at least 6 but not more than 10 carbon atoms. Each of $R^{404}$, $R^{405}$ and $R^{406}$ independently represents at least one group selected from the group consisting of a hydrogen, an amino group, a carbamide group (—NHCONH$_2$), groups represented by general formula (II-1) shown above, groups represented by general formula (II-2) shown above, groups represented by general formula (II-3) shown above, and groups represented by general formula (II-4) shown above.

The divalent aliphatic hydrocarbon group of at least 1 but not more than 10 carbon atoms or the divalent aromatic cyclic group of at least 6 but not more than 10 carbon atoms for $Y^{404}$, $Y^{405}$ and $Y^{406}$ is as described above for the divalent aliphatic hydrocarbon group of at least 1 but not more than 10 carbon atoms or the divalent aromatic cyclic group of at least 6 but not more than 10 carbon atoms for $Y^{401}$ in general formula (IV-I).

Specific preferred examples of the compound (IV-III) include the compounds represented by formulas (B-31) to (B-317) shown below.

[Chemical formula 50]

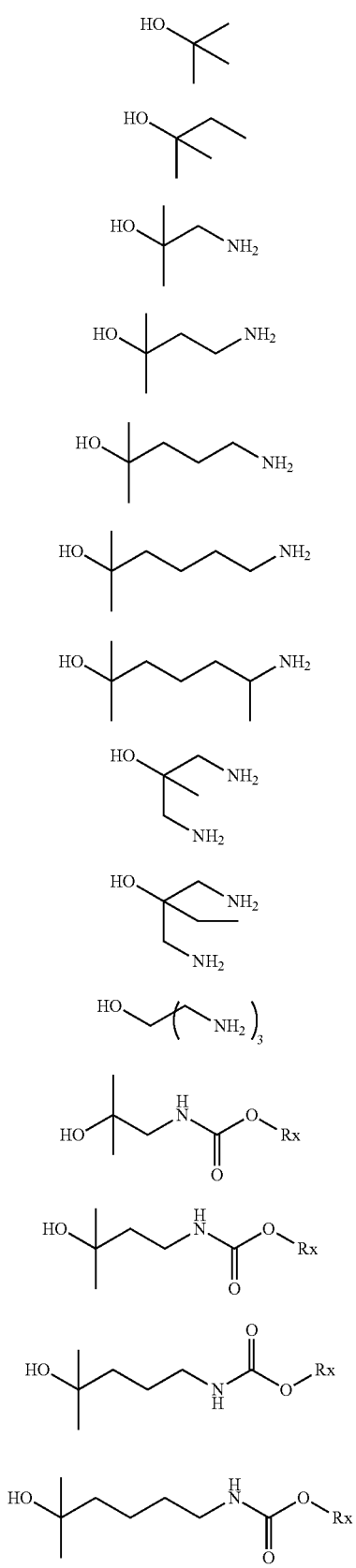

(B-31)
(B-32)
(B-33)
(B-34)
(B-35)
(B-36)
(B-37)
(B-38)
(B-39)
(B-310)
(B-311)
(B-312)
(B-313)
(B-314)

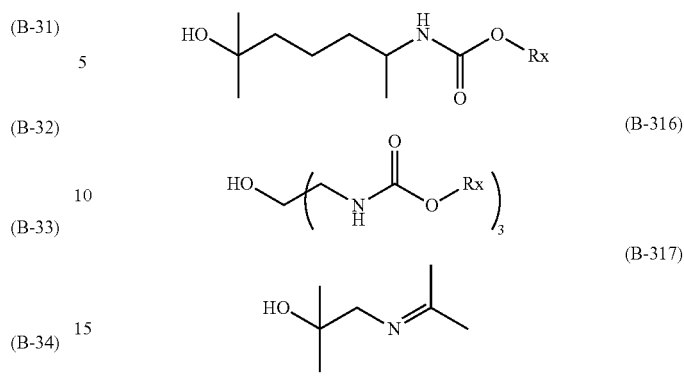

(B-315)
(B-316)
(B-317)

(Rx in the above formulas is preferably a methyl group, ethyl group, propyl group (including structural isomers), butyl group (including structural isomers), pentyl group (including structural isomers), hexyl group (including structural isomers), pentyl group (including structural isomers), octyl group (including structural isomers), phenyl group, methylphenyl group (including structural isomers), dimethylphenyl group (including structural isomers), ethylphenyl group (including structural isomers), and diethylphenyl group (including structural isomers)).

[Compound (IV-IV)]

The compound (IV-IV) is a compound represented by general formula (IV-IV) shown below. The compound (IV-IV) may exist in the form of a salt with an acid. The acid that forms the salt with the compound (IV-IV) is as described above for the acid that forms a salt with the compound (IV-1),

[Chemical formula 51]

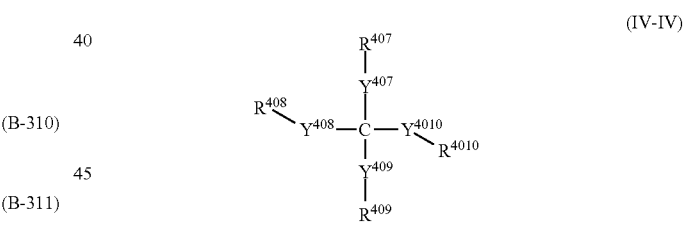

(IV-IV)

In general formula (IV-1V), each of $Y^{407}$, $Y^{408}$, $Y^{409}$ and $Y^{4010}$ represents a divalent aliphatic hydrocarbon group of at least 1 but not more than 10 carbon atoms or a divalent aromatic cyclic group of at least 6 but not more than 10 carbon atoms. At least one of $R^{407}$, $R^{408}$, $R^{409}$ and $R^{4010}$ represents a hydroxyl group, and each of the others represents at least one group selected from the group consisting of a hydrogen, an amino group, a carbamide group (—$NHCONH_2$), groups represented by general formula (II-1) shown above, groups represented by general formula (II-2) shown above, groups represented by general formula (II-3) shown above, and groups represented by general formula (II-4) shown above.

The divalent aliphatic hydrocarbon group of at least 1 but not more than 10 carbon atoms or the divalent aromatic cyclic group of at least 6 but not more than 10 carbon atoms for $Y^{407}$, $Y^{408}$, $Y^{409}$ and $Y^{4010}$ is as described above for the divalent aliphatic hydrocarbon group of at least 1 but not more than 10 carbon atoms or the divalent aromatic cyclic group of at least 6 but not more than 10 carbon atoms for $Y^{401}$ in general formula (IV-I).

Specific preferred examples of the compound (IV-IV) include the compound represented by formula (B-41) shown below.

[Chemical formula 52]

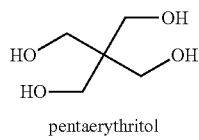

(B-41)

pentaerythritol

[Acid Catalyst]

The acid catalyst may be any acid with a normal boiling point of 0° C. or higher, and there are no particular limitations. The normal boiling point of the acid catalyst is 0° C. or higher, preferably 10° C. or higher, more preferably 30° C. or higher, and even more preferably 50° C. or higher. By ensuring that the normal boiling point of the acid catalyst is at least as high as the above lower limit, the acid catalyst can be used in a liquid state under the reaction conditions, and loss of the acid by distillation can be more effectively suppressed.

On the other hand, in terms of ensuring favorable viscosity under the reaction conditions, the normal boiling point of the acid catalyst is, for example, typically not higher than 400° C., and for example, may be 350° C. or lower.

The acid catalyst may be an organic acid or an inorganic acid.

Examples of organic acids include aliphatic sulfonic acids, aromatic sulfonic acids, alkyl phosphoric acids, alkyl sulfuric acids, and aromatic sulfuric acids.

Specific examples of the aliphatic sulfonic acids include methanesulfonic acid, and the like.

Specific examples of the aromatic sulfonic acids include p-toluenesulfonic acid (normal boiling point: 140° C.) and trifluoromethanesulfonic acid (normal boiling point: 162° C.).

Specific examples of the alkyl phosphoric acids include dimethyl phosphate (normal boiling point: 174° C.) and diethyl phosphate (normal boiling point: 204° C.).

Specific examples of the alkyl sulfuric acids include dimethyl sulfate (normal boiling point: 188° C.), diethyl sulfate (normal boiling point: 209° C.) and lauryl sulfuric acid (normal boiling point: 206° C.).

Specific examples of aromatic sulfate esters include phenyl sulfate and phenyl fluorosulfate.

Examples of the inorganic acids include sulfuric acid (normal boiling point: 337° C.), phosphoric acid (normal boiling point: 158° C.), nitric acid (normal boiling point: 83° C.) and boric acid (normal boiling point: 300° C.).

One of these acids may be used alone, or a combination of two or more acids may be used.

The inventors of the present invention discovered that in the production method of the present invention, when producing the amino acid aminoalkyl ester and the inorganic acid salt thereof, among the various possibilities listed above for the acid catalyst, an aliphatic sulfonic acid or an inorganic acid is preferred, and methanesulfonic acid, p-toluenesulfonic acid, trifluoromethanesulfonic acid, sulfuric acid, phosphoric acid, or a combination of these acids is more preferred.

The reason for this preference is that by using these acids, side reactions of the above compound (IV) can be suppressed, enabling the yield of the amino acid aminoalkyl ester or the inorganic acid salt thereof to be improved, and the reason for this yield improvement is thought to be due to factors such as the molecular structure and molecular size of these acids, the dipole moment and the acid dissociation constant expressed by pKa, with these physical properties contributing to a suppression of side reactions including modifications of the substrate itself, while specifically promoting the main reaction.

[Carrying Agent]

In the production method of the present embodiment, a carrying agent may be used to assist the distillation of the water or hydroxy compound produced by the reaction. Here, a "carrying agent" refers to a substance which is substantially inert and exists in the gaseous state under the reaction conditions. Further, the expression "substantially inert" means that under the conditions in which synthesis of the amino acid aminoalkyl ester or the inorganic acid salt thereof is conducted, the substance does not react with the raw materials, including the compound (I) or the compound (III) or the salt thereof, and the at least one compound selected from the group consisting of the compound (IV-I), the compound (IV-II), the compound (IV-III) and the compound (IV-IV), or the salt thereof, nor with the amino acid aminoalkyl ester or the inorganic acid salt thereof and the water that represent the reaction products, or if reaction does occur, then there is no significant effect on the synthesis of the amino acid aminoalkyl ester or the inorganic acid salt thereof.

Specific examples of this type of carrying agent include inert gases and organic solvents and the like.

(Inert Gas)

Examples of the inert gas include nitrogen, argon, helium, carbon dioxide gas, methane, ethane and propane. Among these, an inert gas such as nitrogen is preferred as the carrying agent.

(Organic Solvent)

The organic solvent is preferably a solvent that undergoes azeotropic distillation with water. The organic solvent may be supplied in a solution state, or supplied to the reaction system in a gaseous state.

Examples of this type of organic solvent include aliphatic solvents, alicyclic solvents, aromatic solvents which may have a substituent, unsubstituted hydrocarbon solvents, and mixtures of these solvents.

Further, compounds which may have an oxygen atom such as ethers, ketones and esters may be used, and compounds which may have a sulfur atom such as thioethers, sulfoxides and sulfones may also be used.

Specific examples of the organic solvent includes alkanes, aromatic hydrocarbons and alkyl-substituted aromatic hydrocarbons, aromatic compounds substituted with a nitro group or a halogen, polycyclic hydrocarbon compounds, alicyclic hydrocarbons, ketones, esters, ethers and thioethers, sulfoxides, sulfones, and silicone oils.

Examples of the alkanes include hexane, heptane, octane, nonane, decane, n-hexadecane, n-octadecane, eicosane and squalane.

Examples of the aromatic hydrocarbons and alkyl-substituted aromatic hydrocarbons include benzene, toluene, xylene, ethylbenzene, triethylbenzene, cumene, diisopropylbenzene, dibutylbenzene, naphthalene, lower alkyl-substituted naphthalene, and dodecylbenzene.

Examples of the aromatic compounds substituted with a nitro group or a halogen include chlorobenzene, 4-methylbenzyl chloride, p-dichlorobenzene, bromobenzene, dibromobenzene, chloronaphthalene, bromonaphthalene, nitrobenzene and nitronaphthalene.

Examples of the polycyclic hydrocarbon compounds include diphenyl, substituted diphenyl, diphenylmethane, terphenyl, anthracene, phenanthrene, benzyltoluene, benzyltoluene isomers, and triphenylmethane.

Examples of the alicyclic hydrocarbons include cyclohexane and ethylcyclohexane.

Examples of the ketones include methyl ethyl ketone and acetophenone.

Examples of the esters include dibutyl phthalate, dihexyl phthalate and dioctyl phthalate.

Examples of the ethers and thioethers include diphenyl ether and diphenyl sulfide.

Examples of the sulfoxides include dimethyl sulfoxide and diphenyl sulfoxide.

Examples of the sulfones include dimethyl sulfone, diethyl sulfone, diphenyl sulfone and sulfolane.

Among these, the inert solvent is preferably an aromatic hydrocarbon, an alkyl-substituted aromatic hydrocarbon, or an aromatic compound substituted with a nitro group or a halogen, is more preferably an alkyl-substituted aromatic hydrocarbon or an aromatic compound substituted with a halogen, and is even more preferably toluene, xylene or p-dichlorobenzene.

The amount supplied of the carrying agent, for example in the case where the carrying agent is supplied in a solution state, may be set to an amount of at least 0.01 times but not more than 1.0 times, and preferably at least 0.02 times but not more than 0.5 times, the volume of the reaction liquid per hour. Further, when the carrying agent is supplied in the gaseous state, the amount supplied may be set to an amount of at least 3.0 times but not more than 20.0 times, and preferably at least 5.0 times but not more than 10.0 times, the volume of the reaction liquid per hour.

[Amino Acid Aminoalkyl Ester or Inorganic Acids Salt Thereof]

The amino acid aminoalkyl ester or the inorganic acid salt thereof obtained using the production method of the present embodiment is a compound represented by general formula (I) shown above or a compound represented by general formula (III) shown above, in which $R^{13}$ or $R^{33}$ has been substituted with a group obtained by removing the hydroxyl group from general formula (IV-I), (IV-II), (IV-III) or (IV-IV) shown above, or is an inorganic acid salt of that compound. For example, in those cases where the group obtained by removing the hydroxyl group from general formula (IV-I) is —$(CH_2)_{n41}$—$R^{41}$, a compound represented by general formula (I)' shown below, a compound represented by general formula (III)' shown below or an inorganic acid salt thereof is obtained.

[Chemical formula 53]

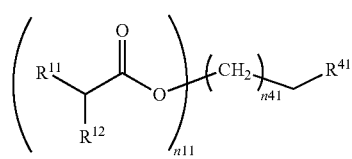

(I)'

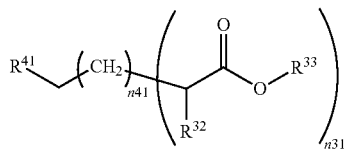

(III)'

In general formula (I)', $R^{11}$ and $R^{12}$ are the same as $R^{11}$ and $R^{12}$ respectively in general formula (I) described above. $R^{41}$ and n41 are the same as $R^{41}$ and n41 respectively in general formula (I) described above.

In general formula (III)', $R^{32}$ and $R^{33}$ are the same as $R^{32}$ and $R^{33}$ respectively in general formula (III) described above. $R^{41}$ and n41 are the same as $R^{41}$ and n41 respectively in general formula (I) described above.

EXAMPLES

Embodiments of the present invention are described below in further detail using specific examples, but the embodiments of the present invention are in no way limited by the following examples, provided they do not exceed the scope of the invention.

[Synthesis Example 1] Synthesis of Compound (A-20)

A glass flask with an internal capacity of 500 mL was charged with 200 g of lysine monohydrochloride, 34 g of urea and 100 g of water, and the resulting mixture was heated at 120° C. for 2 hours while being stirred under a nitrogen atmosphere at atmospheric pressure. The reaction liquid was then cooled, the reaction liquid was poured into 2-propanol, and the precipitated solid was collected by filtration. Analysis by $^1$H-NMR revealed that the collected solid was a compound in which the amino group of the lysine had been substituted with a urea linkage. This compound was used as compound (A-20) as a raw material in Example 22 described below.

[Example 1] Production of Compound (E-1)

A glass flask with an internal capacity of 1,000 mL fitted with a distillation device was charged with 200 g of a compound (A-1) (glycine) shown as the raw material 1 in Table 1 below, 171 g of a compound (B-1) (ethanolamine) shown as the raw material 2 in Table 1 below, 200 g of toluene and 214 g of phosphoric acid, and a reaction was conducted under reduced pressure at 100° C., with the toluene being distilled off while additional toluene was added to keep the liquid level substantially constant. After continuing the reaction for 8 hours, collection of the reaction liquid and analysis by liquid chromatography revealed that a compound (E-1) shown as the product in Table 1 below had been produced at a yield of 84% relative to the amount added of the compound (A-1) (glycine). Analysis of the amount of phosphoric acid contained in the compound (E-1) (excluding the counter anion component) by a conventional method revealed 350 wtppm of phosphoric acid relative to the compound (E-1).

[Examples 2 to 48] Production of Compound (E-2) to Compound (E-48)

With the exceptions of adding the raw material 1, the raw material 2 and the solvent in the combinations shown below in Tables 1 to 8, and setting the reaction temperature, pressure and time as shown below in Tables 1 to 8, the same method as Example 1 was used to produce compounds (E-2) to (E-48).

Comparative Example 1

With the exception of replacing the acid used in Example 9 from phosphoric acid to hydrogen chloride, a reaction was conducted using the same method as Example 9. The method for supplying the hydrogen chloride involved supplying hydrogen chloride gas from a hydrogen chloride cylinder using a flow meter that used a corrosion-resistant material of stainless steel or glass, introducing the hydrogen chloride gas into the reaction system while controlling the supply rate and conducting the reaction by bubbling the gas through the liquid phase, and following completion of the reaction, calculating the amount of hydrogen chloride gas introduced into the system to calculate the weight of hydrogen chloride supplied. In this reaction, the yield of the produced compound (E-9) was 55%.

Comparative Example 2

With the exception of replacing the acid used in Example 10 from methanesulfonic acid to hydrogen chloride, a reaction was conducted using the same method as Example 10. The hydrogen chloride was supplied to the reaction system using the same method as Comparative Example 1. In this reaction, the yield of the produced compound (E-10) was 50%.

TABLE 1

| | | Raw material 1: Compound (I) or Compound (III) | | |
|---|---|---|---|---|
| Examples | Compound | Structural formula | Amount added (g) | Molecular weight |
| Example 1 | A-1 | H₂N-CH₂-C(=O)-OH | 200 | 75 |
| Example 2 | A-1 | H₂N-CH₂-C(=O)-OH | 200 | 75 |
| Example 3 | A-2 | (CH₃)₂C=N-CH₂-C(=O)-OH | 200 | 75 |
| Example 4 | A-3 | PhO-C(=O)-NH-CH₂-C(=O)-OH | 200 | 75 |
| Example 5 | A-4 | H₂N-CH(CH₃)-C(=O)-OH | 200 | 89 |
| Example 6 | A-4 | H₂N-CH(CH₃)-C(=O)-OH | 200 | 89 |
| Example 7 | A-5 | 1,3,5-tris(aminocarboxymethyl)benzene | 150 | 297 |

TABLE 1-continued

| | | Raw material 2: Compound (IV-I) to (IV-IV) | | | |
|---|---|---|---|---|---|
| Examples | Compound | Structural formula | Amount added (g) | Molecular weight | molar ratio |
| Example 1 | B-1 | HO\~\~NH$_2$ | 170 | 61 | 0.96 |
| Example 2 | B-2 | HO\~\~NH$_2$ ·H$_3$PO$_4$ | 430 | 159 | 0.99 |
| Example 3 | B-2 | HO\~\~NH$_2$ ·H$_3$PO$_4$ | 430 | 159 | 0.99 |
| Example 4 | B-2 | HO\~\~NH$_2$ ·H$_3$PO$_4$ | 430 | 159 | 0.99 |
| Example 5 | B-1 | HO\~\~NH$_2$ | 143 | 61 | 0.96 |
| Example 6 | B-1 | HO\~\~NH$_2$ | 143 | 61 | 0.96 |
| Example 7 | B-3 | HO\~CH(CH$_3$)\~NH$_2$ | 119 | 75 | 0.32 |

| | Acid | | Solvent | | Reaction conditions | | |
|---|---|---|---|---|---|---|---|
| Examples | Compound name | Amount added (g) | Compound name | Amount added (g) | Temperature (°C.) | Pressure (kPa) | Time (hr) |
| Example 1 | phosphoric acid | 214 | toluene | 200 | 100 | 80 | 8 |
| Example 2 | phosphoric acid | 210 | toluene | 200 | 100 | 80 | 10 |
| Example 3 | phosphoric acid | 210 | toluene | 200 | 100 | 80 | 10 |
| Example 4 | phosphoric acid | 210 | toluene | 200 | 100 | 80 | 10 |
| Example 5 | phosphoric acid | 180 | toluene | 200 | 100 | 80 | 8 |
| Example 6 | sulfuric acid | 270 | toluene | 200 | 100 | 80 | 8 |
| Example 7 | p-toluene sulfonic acid | 432 | o-dichloro benzene | 100 | 110 | 10 | 6 |

| | Product | | Yield (%) | Amount of acid in product wt % |
|---|---|---|---|---|
| Examples | Compound | Structural formula | | |
| Example 1 | E-1 | H$_2$N\~C(=O)\~O\~\~NH$_2$ | 84 | 0.05 |
| Example 2 | E-2 | H$_2$N\~C(=O)\~O\~\~NH$_2$ | 82 | 0.03 |
| Example 3 | E-3 | (CH$_3$)$_2$C=N\~CH$_2$\~C(=O)\~O\~\~NH$_2$ | 82 | 0.08 |

TABLE 1-continued

| Example 4 | E-4 | [structure: phenyl-O-C(=O)-NH-CH2-C(=O)-O-CH2CH2-NH2] | 82 | 0.06 |
| Example 5 | E-5 | [structure: H2N-CH2-C(=O)-O-CH2CH2-NH2] | 78 | 0.04 |
| Example 6 | E-6 | [structure: H2N-CH(CH3)-C(=O)-O-CH2CH2-NH2] | 76 | 0.08 |
| Example 7 | E-7 | [structure: 1,3,5-trisubstituted benzene with three -CH(NH2)-C(=O)-O-CH2-CH(CH3)-NH2 groups] | 68 | 0.06 |

TABLE 2

| | | Raw material 1: Compound (I) or Compound (III) | | |
|---|---|---|---|---|
| Examples | Compound | Structural formula | Amount added (g) | Molecular weight |
| Example 8 | A-6 | [structure: 1-naphthyl-CH(NH2)-COOH] | 150 | 201 |
| Example 9 | A-7 | [structure: H2N-(CH2)4-CH(NH2)-COOH · HCl (lysine HCl)] | 200 | 182 |
| Example 10 | A-8 | [structure: phenyl-CH2-CH(NH2)-COOH (phenylalanine)] | 150 | 223 |

TABLE 2-continued

| Example | | Structural formula | | |
|---|---|---|---|---|
| Example 11 | A-9 | phenylalanine methyl ester with methyl carbamate (NH-C(O)-OCH3) | 150 | 223 |
| Example 12 | A-10 | methyl 2-(ethylthio)-2-ureidoacetate | 300 | 178 |
| Example 13 | A-11 | glutamic acid | 130 | 147 |
| Example 14 | A-12 | tert-butyl 2-amino-3-(4-isopropylphenyl)propanoate | 300 | 207 |

Raw material 2:
Compound (IV-I) to (IV-IV)

| Examples | Compound | Structural formula | Amount added (g) | Molecular weight | molar ratio |
|---|---|---|---|---|---|
| Example 8 | B-4 | HO-CH2CH2-NH-C(O)-NH-CH2CH2-OH | 57 | 148 | 1.94 |
| Example 9 | B-1 | HO-CH2CH2-NH2 | 70 | 61 | 0.96 |
| Example 10 | B-5 | PhO-C(O)-NH-CH2CH2-OH | 120 | 181 | 1.01 |
| Example 11 | B-5 | PhO-C(O)-NH-CH2CH2-OH | 120 | 181 | 1.01 |
| Example 12 | B-4 | HO-CH2CH2-NH-C(O)-NH-CH2CH2-OH | 121 | 148 | 2.06 |

TABLE 2-continued

| Examples | | | | | | |
|---|---|---|---|---|---|---|
| Example 13 | B-6 | 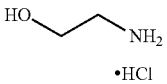 HO~~NH2·HCl | | 181 | 97 | 0.47 |
| Example 14 | B-7 | 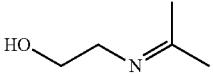 HO~~N=C(CH3)2 | | 138 | 101 | 1.06 |

| | Acid | | Solvent | | Reaction conditions | | |
|---|---|---|---|---|---|---|---|
| Examples | Compound name | Amount added (g) | Compound name | Amount added (g) | Temperature (°C.) | Pressure (kPa) | Time (hr) |
| Example 8 | trifluoro-methane sulfonic acid | 134 | o-dichloro benzene | 200 | 100 | 10 | 8 |
| Example 9 | phosphoric acid | 130 | toluene | 200 | 100 | 80 | 8 |
| Example 10 | methane sulfonic acid | 277 | toluene | 200 | 100 | 80 | 8 |
| Example 11 | methane sulfonic acid | 277 | toluene | 200 | 100 | 80 | 8 |
| Example 12 | phosphoric acid | 46 | xylene | 300 | 130 | 40 | 5 |
| Example 13 | phosphoric acid | 348 | xylene | 100 | 130 | 40 | 8 |
| Example 14 | sulfuric acid | 147 | toluene | 200 | 100 | 80 | 10 |

| Examples | Compound | Structural formula | Yield (%) | Amount of acid in product wt % |
|---|---|---|---|---|
| Example 8 | E-8 | 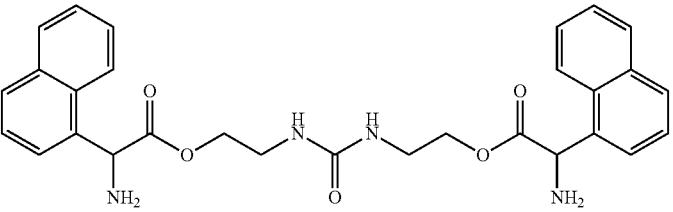 [SMILES: NC(C(=O)OCCNC(=O)NCCOC(=O)C(N)c1cccc2ccccc12)c1cccc2ccccc12] | 73 | 0.04 |
| Example 9 | E-9 | 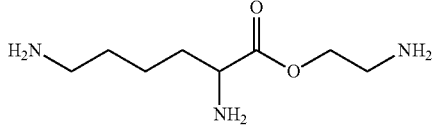 [SMILES: NCCCCC(N)C(=O)OCCN] | 79 | 0.05 |
| Example 10 | E-10 | 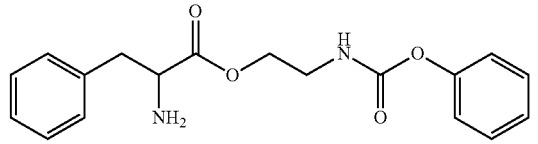 [SMILES: NC(Cc1ccccc1)C(=O)OCCNC(=O)Oc1ccccc1] | 73 | 0.06 |
| Example 11 | E-11 | 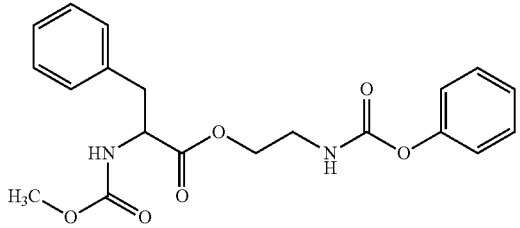 [SMILES: COC(=O)NC(Cc1ccccc1)C(=O)OCCNC(=O)Oc1ccccc1] | 73 | 0.07 |

TABLE 2-continued

| Example 12 | E-12 | [structure: bis-carbamate with ethylthio, urea linker] | 83 | 0.06 |
| Example 13 | E-13 | [structure: glutamic acid bis(2-aminoethyl) ester] | 79 | 0.04 |
| Example 14 | E-14 | [structure: 4-isopropylphenylalanine 2-(isopropylideneamino)ethyl ester] | 78 | 0.08 |

TABLE 3

| | | Raw material 1: Compound (I) or Compound (III) | | |
| --- | --- | --- | --- | --- |
| Examples | Compound | Structural formula | Amount added (g) | Molecular weight |
| Example 15 | A-13 | [structure: C₈H₁₇-CH(NH₂)-C(O)-O-tBu] | 200 | 187 |
| Example 16 | A-14 | [structure: N,N'-bis-phenoxycarbonyl lysine tert-butyl ester] | 200 | 442 |

TABLE 3-continued

| Examples | Compound | Structural formula | Amount added (g) | Molecular weight |
|---|---|---|---|---|
| Example 17 | A-15 | (phenyl carbamate lysine derivative with two phenyloxycarbonyl groups) | 300 | 386 |
| Example 18 | A-16 | (N-butoxycarbonyl leucine) | 150 | 231 |
| Example 19 | A-17 | (urea-bis-alanine dicarboxylic acid) | 150 | 204 |
| Example 20 | A-18 | (N-isopropylidene phenylalanine) | 150 | 205 |
| Example 21 | A-19 | (isopropoxycarbonyl alanine) | 200 | 175 |
| Example 22 | A-20 | (bis-urea lysine derivative with t-butyl groups) | 150 | — |

| Examples | Compound | Raw material 2: Compound (IV-I) to (IV-IV) Structural formula | Amount added (g) | Molecular weight | molar ratio |
|---|---|---|---|---|---|
| Example 15 | B-8 | (amino alcohol · HCl) | 179 | 181 | 1.08 |

TABLE 3-continued

| Example | | Structure | | | |
|---|---|---|---|---|---|
| Example 16 | B-5 | phenyl carbamate of 2-aminoethanol (PhO-C(=O)-NH-CH$_2$CH$_2$-OH) | 135 | 181 | 0.61 |
| Example 17 | B-5 | phenyl carbamate of 2-aminoethanol (PhO-C(=O)-NH-CH$_2$CH$_2$-OH) | 135 | 181 | 1.04 |
| Example 18 | B-9 | HO-CH$_2$CH$_2$-NH-C(=O)-NH-C$_4$H$_9$ | 114 | 160 | 0.91 |
| Example 19 | B-4 | HO-CH$_2$CH$_2$-NH-C(=O)-NH-CH$_2$CH$_2$-OH | 239 | 148 | 0.46 |
| Example 20 | B-7 | HO-CH$_2$CH$_2$-N=C(CH$_3$)$_2$ | 78 | 101 | 0.95 |
| Example 21 | B-8 | HO-CH$_2$CH$_2$-NH-C(=O)-O-CH(CH$_3$)$_2$ | 143 | 147 | 1.1 |
| Example 22 | B-5 | phenyl carbamate of 2-aminoethanol (PhO-C(=O)-NH-CH$_2$CH$_2$-OH) | 103 | 181 | 1.1 relative to carboxy |

| | Acid | | Solvent | | Reaction conditions | | |
|---|---|---|---|---|---|---|---|
| Examples | Compound name | Amount added (g) | Compound name | Amount added (g) | Temperature (°C.) | Pressure (kPa) | Time (hr) |
| Example 15 | sulfuric acid | 106 | toluene | 200 | 100 | 80 | 10 |
| Example 16 | phosphoric acid | 181 | toluene | 200 | 100 | 80 | 10 |
| Example 17 | phosphoric acid | 181 | toluene | 200 | 100 | 80 | 10 |
| Example 18 | phosphoric acid | 173 | xylene | 300 | 130 | 40 | 5 |
| Example 19 | phosphoric acid | 46 | xylene | 200 | 130 | 40 | 5 |
| Example 20 | methane sulfonic acid | 40 | toluene | 200 | 100 | 80 | 8 |
| Example 21 | phosphoric acid | 180 | toluene | 200 | 100 | 80 | 8 |
| Example 22 | phosphoric acid | 139 | toluene | 200 | 100 | 80 | 10 |

| | | Product | | Amount |
|---|---|---|---|---|
| Examples | Compound | Structural formula | Yield (%) | of acid in product wt % |
| Example 15 | E-15 | C$_8$H$_17$-CH(NH$_2$)-C(=O)-O-C(CH$_3$)$_2$-CH$_2$CH$_2$-CH(CH$_3$)-NH$_2$ | 79 | 0.05 |

TABLE 3-continued

| | | | | |
|---|---|---|---|---|
| Example 16 | E-16 | (structure) | 80 | 0.06 |
| Example 17 | E-17 | (structure) | 81 | 0.07 |
| Example 18 | E-18 | (structure) | 82 | 0.06 |
| Example 19 | E-19 | (structure) | 81 | 0.04 |
| Example 20 | E-20 | (structure) | 79 | 0.03 |
| Example 21 | E-21 | (structure) | 80 | 0.04 |

TABLE 3-continued

| Examples | Compound | Structural formula | | |
|---|---|---|---|---|
| Example 22 | E-22 | [structure: urea-linked ornithine derivative with phenyl carbamate ester] | 81 | 0.05 |

TABLE 4

Raw material 1: Compound (I) or Compound (III)

| Examples | Compound | Structural formula | Amount added (g) | Molecular weight |
|---|---|---|---|---|
| Example 23 | A-21 | [structure: bis-phenyl carbamate lysine derivative] | 150 | 260 |
| Example 24 | A-21 | [structure: bis-phenyl carbamate lysine derivative] | 200 | 386 |
| Example 25 | A-21 | [structure: bis-phenyl carbamate lysine derivative] | 200 | 386 |

TABLE 4-continued
| Examples | Compound | Structural formula | Amount added (g) | Molecular weight | molar ratio |
|---|---|---|---|---|---|
| Example 26 | A-21 | 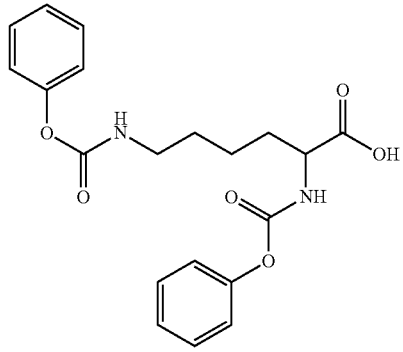 [SMILES: O=C(NCCCCC(NC(=O)Oc1ccccc1)C(=O)O)Oc1ccccc1] | 200 | 386 | |
| Example 27 | A-21 | 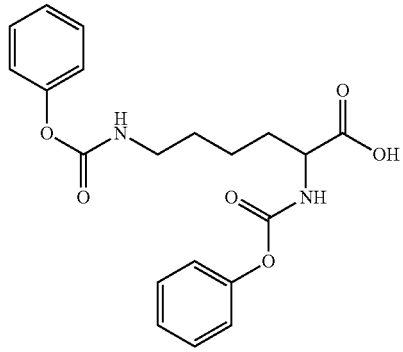 [SMILES: O=C(NCCCCC(NC(=O)Oc1ccccc1)C(=O)O)Oc1ccccc1] | 300 | 386 | |
Raw material 2:
Compound (IV-I) to (IV-IV)
| Examples | Compound | Structural formula | Amount added (g) | Molecular weight | molar ratio |
|---|---|---|---|---|---|
| Example 23 | B-5 | 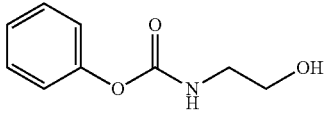 [SMILES: O=C(NCCO)Oc1ccccc1] | 103 | 181 | 1.01 |
| Example 24 | B-9 | 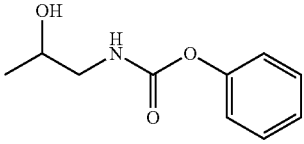 | 41 | 75 | 0.95 |
| Example 25 | B-10 | 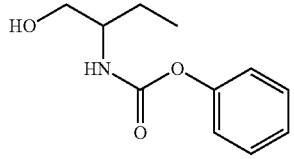 | 48 | 89 | 0.96 |
| Example 26 | B-11 | 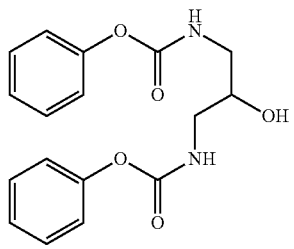 [SMILES: O=C(NCC(O)CNC(=O)Oc1ccccc1)Oc1ccccc1] | 35 | 330 | 4.88 |

TABLE 4-continued

| Example 27 | B-12 | 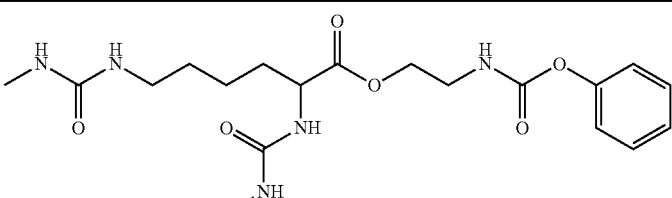 | 50 | 479 | 4.96 |

| | Acid | | Solvent | | Reaction conditions | | |
| --- | --- | --- | --- | --- | --- | --- | --- |
| Examples | Compound name | Amount added (g) | Compound name | Amount added (g) | Temperature (° C.) | Pressure (kPa) | Time (hr) |
| Example 23 | phosphoric acid | 139 | toluene | 200 | 100 | 80 | 10 |
| Example 24 | phosphoric acid | 139 | o-dichloro benzene | 100 | 110 | 10 | 6 |
| Example 25 | phosphoric acid | 139 | o-dichloro benzene | 100 | 110 | 10 | 6 |
| Example 26 | phosphoric acid | 139 | o-dichloro benzene | 100 | 110 | 10 | 6 |
| Example 27 | phosphoric acid | 139 | o-dichloro benzene | 100 | 110 | 10 | 6 |

| | | Product | | Amount |
| --- | --- | --- | --- | --- |
| Examples | Compound | Structural formula | Yield (%) | of acid in product wt % |
| Example 23 | E-23 | 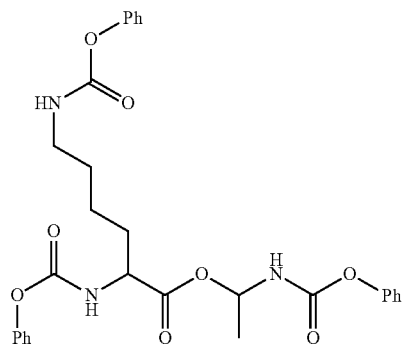 [SMILES: CC(NC(=O)Oc1ccccc1)OC(=O)C(CCCCNC(=O)Oc1ccccc1)NC(=O)Oc1ccccc1] | 80 | 0.06 |
| Example 24 | E-24 | 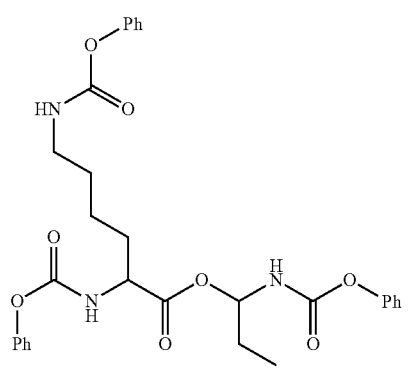 [SMILES: CCC(NC(=O)Oc1ccccc1)OC(=O)C(CCCCNC(=O)Oc1ccccc1)NC(=O)Oc1ccccc1] | 79 | 0.04 |
| Example 25 | E-25 | | 78 | 0.04 |

TABLE 4-continued

| Example 26 | E-26 | [structure: phenyl-O-C(=O)-NH-(CH2)4-CH(NH-C(=O)-O-phenyl)-C(=O)-O-CH(CH2-NH-C(=O)-O-phenyl)(CH2-NH-C(=O)-O-phenyl)] | 77 | 0.05 |
| Example 27 | E-27 | [structure: phenyl-O-C(=O)-NH-(CH2)4-CH(NH-C(=O)-O-phenyl)-C(=O)-O-C(CH2-NH-C(=O)-O-phenyl)3] | 78 | 0.06 |

TABLE 5

| | | Raw material 1: Compound (I) or Compound (III) | | |
|---|---|---|---|---|
| Examples | Compound | Structural formula | Amount added (g) | Molecular weight |
| Example 28 | A-21 | [structure: phenyl-O-C(=O)-NH-(CH2)4-CH(NH-C(=O)-O-phenyl)-COOH] | 200 | 386 |
| Example 29 | A-21 | [structure: phenyl-O-C(=O)-NH-(CH2)4-CH(NH-C(=O)-O-phenyl)-COOH] | 200 | 386 |

TABLE 5-continued
| Example 30 | A-21 | 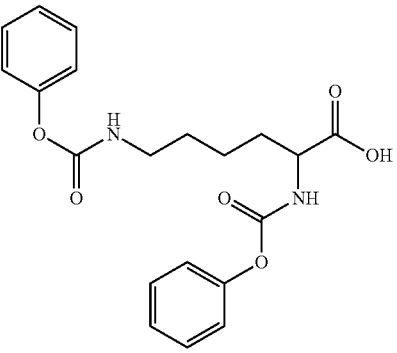 [SMILES: O=C(NCCCCC(NC(=O)Oc1ccccc1)C(=O)O)Oc1ccccc1] | 200 | 386 | |
| Example 31 | A-21 | 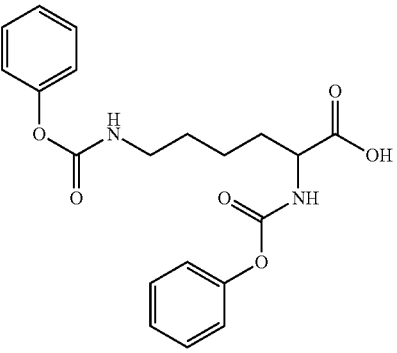 [SMILES: O=C(NCCCCC(NC(=O)Oc1ccccc1)C(=O)O)Oc1ccccc1] | 200 | 386 | |
| Example 32 | A-21 | 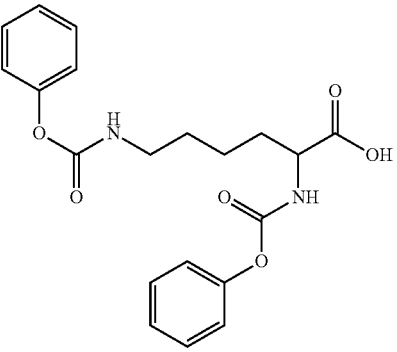 [SMILES: O=C(NCCCCC(NC(=O)Oc1ccccc1)C(=O)O)Oc1ccccc1] | 200 | 386 | |
| | | Raw material 2: Compound (IV-I) to (IV-IV) | | | |
| Examples | Compound | Structural formula | Amount added (g) | Molecular weight | molar ratio |
| Example 28 | B-13 | | 75 | 493 | 3.40 |
| Example 29 | B-9 | | 41 | 75 | 0.95 |

TABLE 5-continued

| Examples | | Structure | | | |
|---|---|---|---|---|---|
| Example 30 | B-10 | 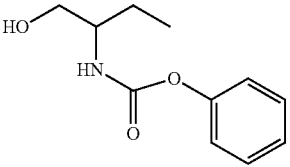 | 48 | 89 | 0.96 |
| Example 31 | B-11 | 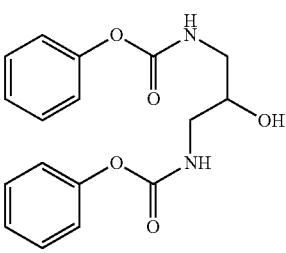 [SMILES: O=C(NCC(O)CNC(=O)Oc1ccccc1)Oc1ccccc1] | 35 | 330 | 4.88 |
| Example 32 | B-12 | 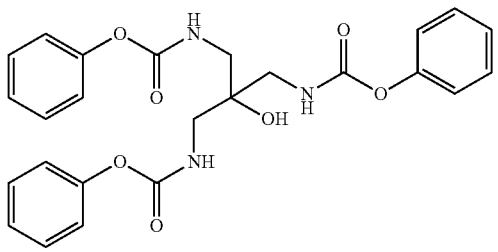 [SMILES: O=C(NCC(O)(CNC(=O)Oc1ccccc1)CNC(=O)Oc1ccccc1)Oc1ccccc1] | 50 | 479 | 4.96 |

| | Acid | | Solvent | | Reaction conditions | | |
|---|---|---|---|---|---|---|---|
| Examples | Compound name | Amount added (g) | Compound name | Amount added (g) | Temperature (° C.) | Pressure (kPa) | Time (hr) |
| Example 28 | phosphoric acid | 139 | o-dichloro benzene | 100 | 110 | 10 | 6 |
| Example 29 | p-toluene sulfonic acid | 432 | o-dichloro benzene | 100 | 110 | 10 | 6 |
| Example 30 | p-toluene sulfonic acid | 432 | o-dichloro benzene | 100 | 110 | 10 | 6 |
| Example 31 | p-toluene sulfonic acid | 432 | o-dichloro benzene | 100 | 110 | 10 | 6 |
| Example 32 | p-toluene sulfonic acid | 432 | o-dichloro benzene | 100 | 110 | 10 | 6 |

TABLE 5-continued

| Examples | Product Compound | Structural formula | Yield (%) | Amount of acid in product wt % |
|---|---|---|---|---|
| Example 28 | E-28 | | 76 | 0.07 |
| Example 29 | E-29 | | 77 | 0.06 |
| Example 30 | E-30 | | 79 | 0.05 |
| Example 31 | E-31 | | 75 | 0.04 |

TABLE 5-continued
| Example 32 | E-32 | 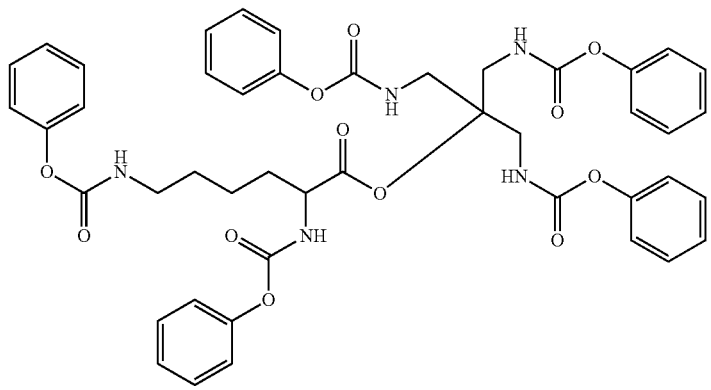 [SMILES: O=C(NCCCCC(NC(=O)Oc1ccccc1)C(=O)OC(CNC(=O)Oc1ccccc1)(CNC(=O)Oc1ccccc1)CNC(=O)Oc1ccccc1)Oc1ccccc1] | 74 | 0.06 |
TABLE 6
Raw material 1:
Compound (I) or Compound (III)
| Examples | Compound | Structural formula | Amount added (g) | Molecular weight |
|---|---|---|---|---|
| Example 33 | A-21 | 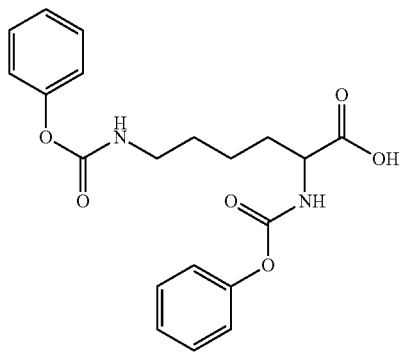 [SMILES: O=C(NCCCCC(NC(=O)Oc1ccccc1)C(=O)O)Oc1ccccc1] | 200 | 386 |
| Example 34 | A-21 | 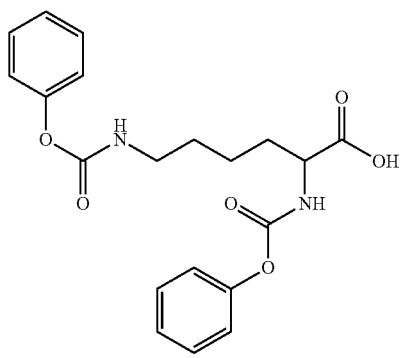 [SMILES: O=C(NCCCCC(NC(=O)Oc1ccccc1)C(=O)O)Oc1ccccc1] | 200 | 386 |

TABLE 6-continued
| | Compound | Structural formula | Amount added (g) | Molecular weight | molar ratio |
|---|---|---|---|---|---|
| Example 35 | A-21 | 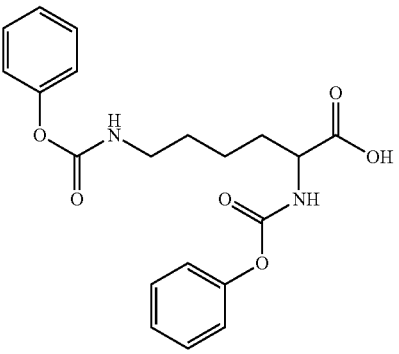 [SMILES: O=C(NCCCCC(NC(=O)Oc1ccccc1)C(=O)O)Oc1ccccc1] | 200 | 386 | |
| Example 36 | A-21 | 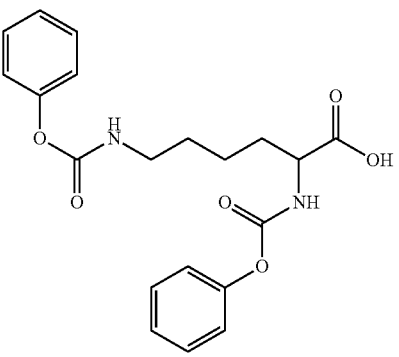 [SMILES: O=C(NCCCCC(NC(=O)Oc1ccccc1)C(=O)O)Oc1ccccc1] | 200 | 386 | |
| Example 37 | A-21 | 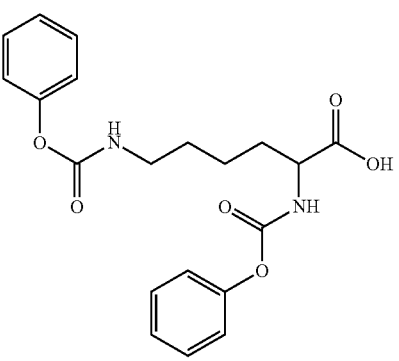 [SMILES: O=C(NCCCCC(NC(=O)Oc1ccccc1)C(=O)O)Oc1ccccc1] | 200 | 386 | |
Raw material 2:
Compound (IV-I) to (IV-IV)
| | Compound | Structural formula | Amount added (g) | Molecular weight | molar ratio |
|---|---|---|---|---|---|
| Example 33 | B-13 | 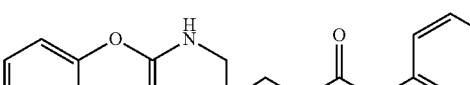 | 75 | 493 | 3.40 |
| Example 34 | B-14 | 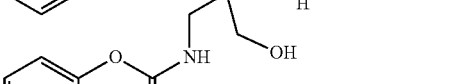 | 41 | 75 | 0.95 |

TABLE 6-continued

| Example 35 | B-15 | 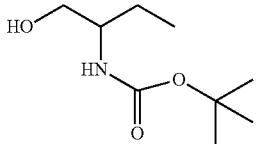 | 48 | 89 | 0.96 |
| Example 36 | B-16 | 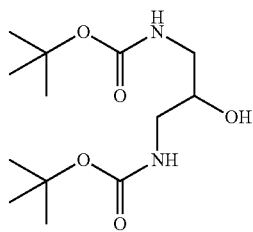 [SMILES: CC(C)(C)OC(=O)NCC(O)CNC(=O)OC(C)(C)C] | 35 | 330 | 4.88 |
| Example 37 | B-17 | 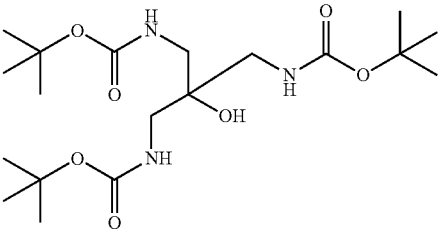 [SMILES: CC(C)(C)OC(=O)NCC(O)(CNC(=O)OC(C)(C)C)CNC(=O)OC(C)(C)C] | 50 | 479 | 4.96 |

| | Acid | | Solvent | | Reaction conditions | | |
| --- | --- | --- | --- | --- | --- | --- | --- |
| Examples | Compound name | Amount added (g) | Compound name | Amount added (g) | Temperature (° C.) | Pressure (kPa) | Time (hr) |
| Example 33 | p-toluene sulfonic acid | 432 | o-dichloro benzene | 100 | 110 | 10 | 6 |
| Example 34 | p-toluene sulfonic acid | 432 | toluene | 200 | 100 | 80 | 10 |
| Example 35 | p-toluene sulfonic acid | 432 | toluene | 200 | 100 | 80 | 10 |
| Example 36 | p-toluene sulfonic acid | 432 | toluene | 200 | 100 | 80 | 10 |
| Example 37 | p-toluene sulfonic acid | 432 | toluene | 200 | 100 | 80 | 10 |

TABLE 6-continued
| Examples | Product Compound | Structural formula | Yield (%) | Amount of acid in product wt % |
|---|---|---|---|---|
| Example 33 | E-33 | 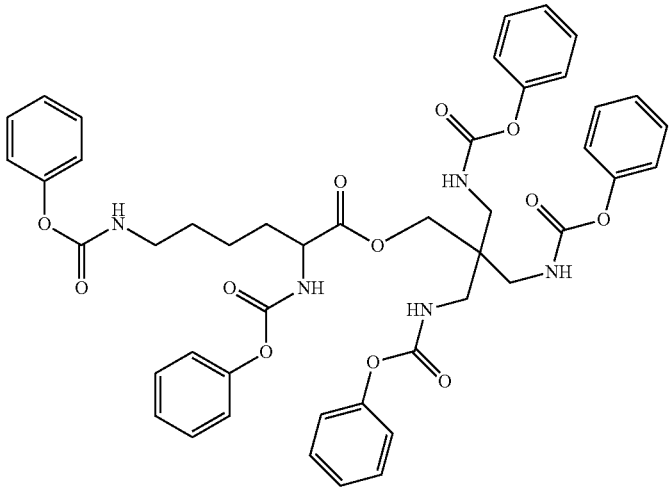 [SMILES: O=C(NCCCCC(NC(=O)Oc1ccccc1)C(=O)OCC(CNC(=O)Oc1ccccc1)(CNC(=O)Oc1ccccc1)CNC(=O)Oc1ccccc1)Oc1ccccc1] | 75 | 0.03 |
| Example 34 | E-34 | 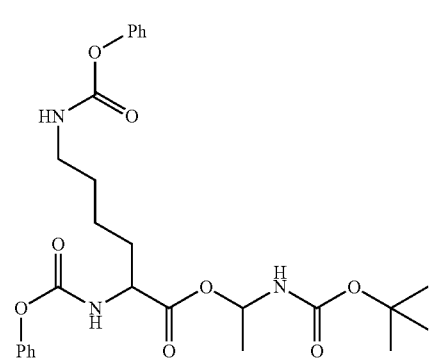 [SMILES: CC(NC(=O)OC(C)(C)C)OC(=O)C(CCCCNC(=O)Oc1ccccc1)NC(=O)Oc1ccccc1] | 80 | 0.04 |
| Example 35 | E-35 | 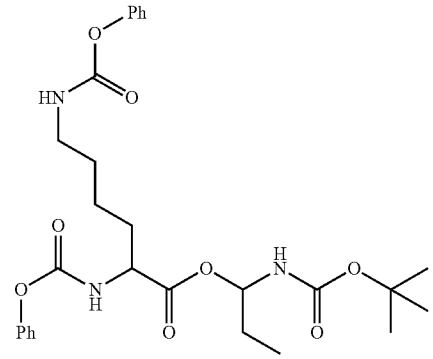 [SMILES: CCC(NC(=O)OC(C)(C)C)OC(=O)C(CCCCNC(=O)Oc1ccccc1)NC(=O)Oc1ccccc1] | 82 | 0.05 |
| Example 36 | E-36 | 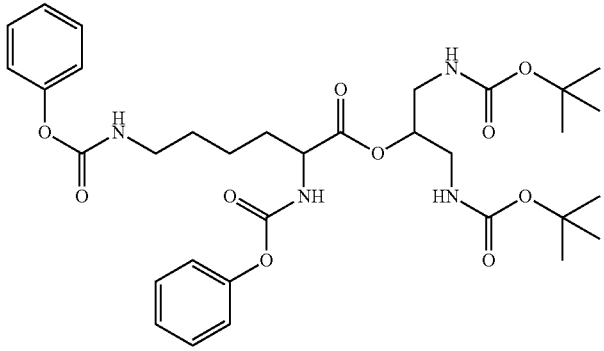 [SMILES: CC(C)(C)OC(=O)NCC(CNC(=O)OC(C)(C)C)OC(=O)C(CCCCNC(=O)Oc1ccccc1)NC(=O)Oc1ccccc1] | 78 | 0.06 |

TABLE 6-continued
| | | | | |
|---|---|---|---|---|
| Example 37 | E-37 | 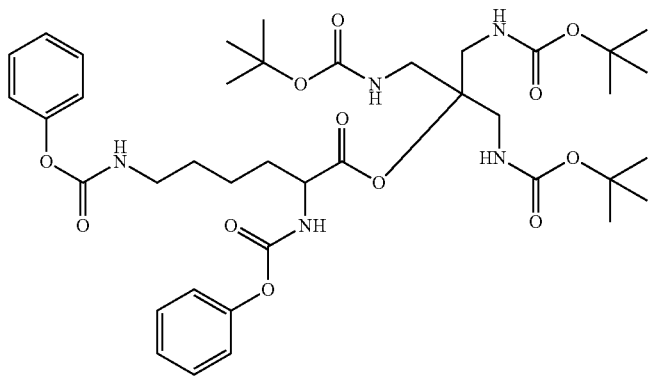 [SMILES: CC(C)(C)OC(=O)NCC(CNC(=O)OC(C)(C)C)(CNC(=O)OC(C)(C)C)OC(=O)C(CCCCNC(=O)Oc1ccccc1)NC(=O)Oc1ccccc1] | 79 | 0.05 |
TABLE 7
| | | Raw material 1: Compound (I) or Compound (III) | | |
|---|---|---|---|---|
| Examples | Compound | Structural formula | Amount added (g) | Molecular weight |
| Example 38 | A-21 | | 200 | 386 |
| Example 39 | A-22 | | 200 | 195 |
| Example 40 | A-22 | | 200 | 195 |
| Example 41 | A-22 | | 200 | 195 |
| Example 42 | A-22 | | 200 | 195 |

TABLE 7-continued

| | | Structural formula | Amount added (g) | Molecular weight | molar ratio |
|---|---|---|---|---|---|
| Example 43 | A-22 | Ph-O-C(=O)-NH-CH2-C(=O)-OH | 200 | 195 | |
| Example 44 | A-22 | Ph-O-C(=O)-NH-CH2-C(=O)-OH | 200 | 195 | |

Raw material 2:
Compound (IV-I) to (IV-IV)

| | Compound | Structural formula | Amount added (g) | Molecular weight | molar ratio |
|---|---|---|---|---|---|
| Example 38 | B-18 | (tri-Boc-aminomethyl compound with OH) | 75 | 493 | 3.40 |
| Example 39 | B-9 | (2-hydroxypropyl phenyl carbamate) | 41 | 75 | 1.87 |
| Example 40 | B-10 | (hydroxymethyl-hydroxyethyl phenyl carbonate) | 48 | 89 | 1.9 |
| Example 41 | B-11 | (bis-phenyl carbamate with OH) | 35 | 330 | 9.66 |
| Example 42 | B-12 | (tris-phenyl carbamate with OH) | 50 | 479 | 9.82 |

TABLE 7-continued

| Example 43 | B-13 | 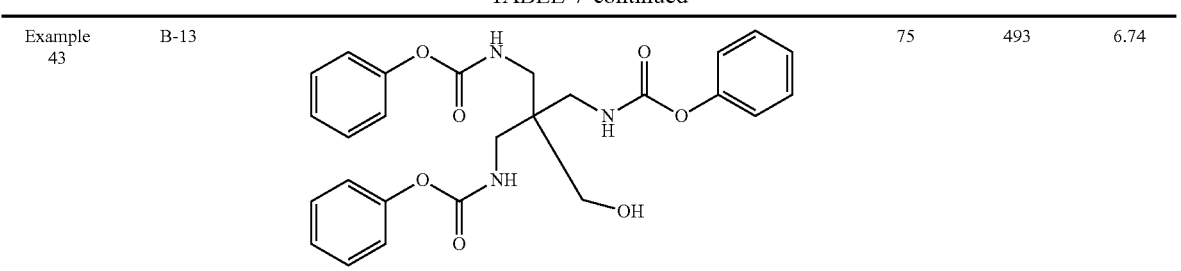 | 75 | 493 | 6.74 |
| Example 44 | B-14 | 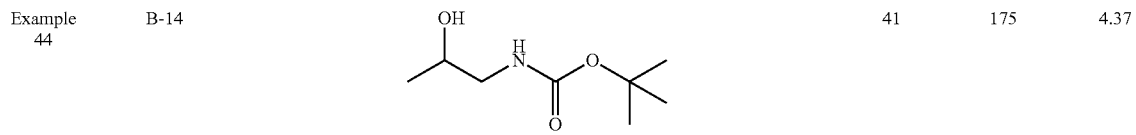 | 41 | 175 | 4.37 |

| Examples | Acid | | Solvent | | Reaction conditions | | |
|---|---|---|---|---|---|---|---|
| | Compound name | Amount added (g) | Compound name | Amount added (g) | Temperature (° C.) | Pressure (kPa) | Time (hr) |
| Example 38 | p-toluene sulfonic acid | 432 | toluene | 200 | 100 | 80 | 10 |
| Example 39 | phosphoric acid | 139 | xylene | 200 | 130 | 40 | 5 |
| Example 40 | phosphoric acid | 139 | xylene | 200 | 130 | 40 | 5 |
| Example 41 | phosphoric acid | 139 | xylene | 200 | 130 | 40 | 5 |
| Example 42 | phosphoric acid | 139 | xylene | 200 | 130 | 40 | 5 |
| Example 43 | phosphoric acid | 139 | xylene | 200 | 130 | 40 | 5 |
| Example 44 | phosphoric acid | 139 | xylene | 200 | 130 | 40 | 5 |

| Examples | Product | | Yield (%) | Amount of acid in product wt % |
|---|---|---|---|---|
| | Compound | Structural formula | | |
| Example 38 | E-38 | 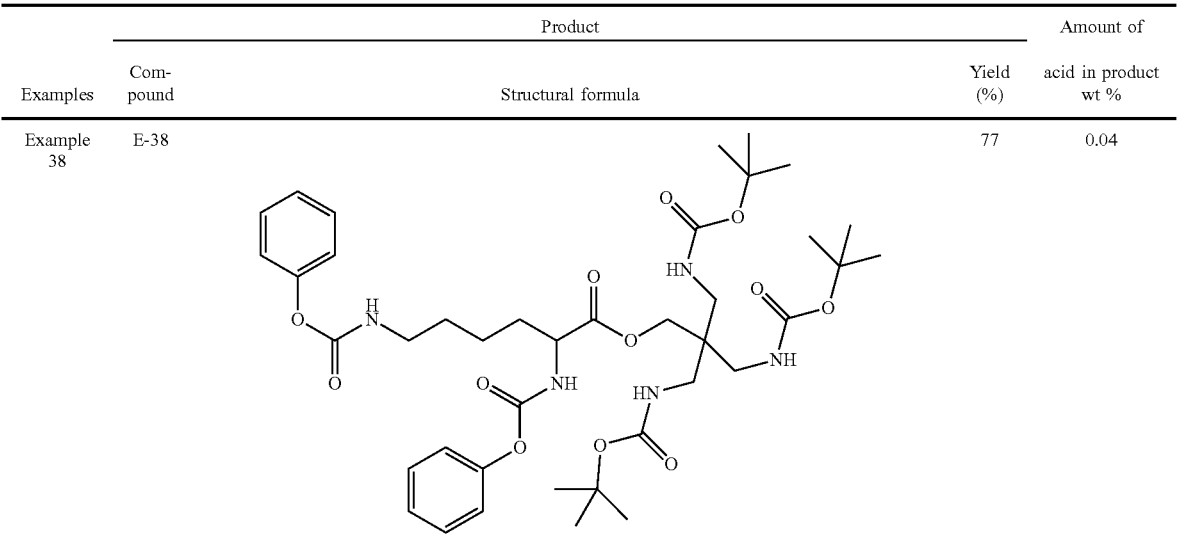 | 77 | 0.04 |
| Example 39 | E-39 | 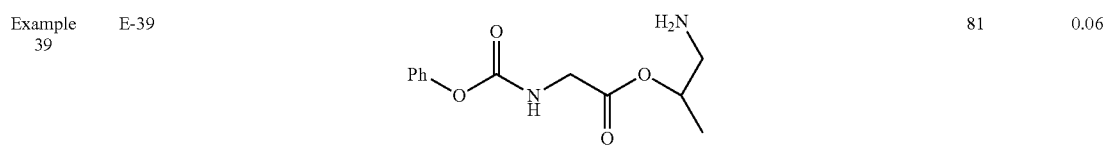 | 81 | 0.06 |
| Example 40 | E-40 | 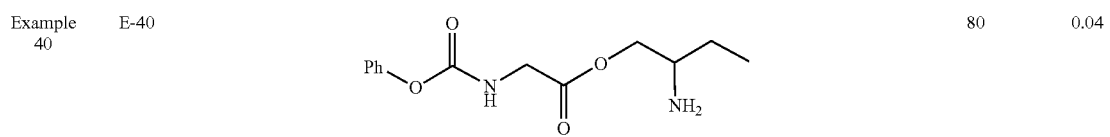 | 80 | 0.04 |

TABLE 7-continued

| Example 41 | E-41 | (structure) | 81 | 0.06 |
| Example 42 | E-42 | (structure) | 80 | 0.06 |
| Example 43 | E-43 | (structure) | 78 | 0.07 |
| Example 44 | E-44 | (structure) | 81 | 0.06 |

TABLE 8

| | | Raw material 1: Compound (I) or Compound (III) | | |
| --- | --- | --- | --- | --- |
| Examples | Compound | Structural formula | Amount added (g) | Molecular weight |
| Example 45 | A-22 | (structure) | 200 | 195 |
| Example 46 | A-22 | (structure) | 200 | 195 |

TABLE 8-continued

| | | Structural formula | Amount added (g) | Molecular weight |
|---|---|---|---|---|
| Example 47 | A-22 | Ph-O-C(=O)-NH-CH2-COOH | 200 | 195 |
| Example 48 | A-22 | Ph-O-C(=O)-NH-CH2-COOH | 200 | 195 |
| Comparative Example 1 | A-7 | H2N-(CH2)4-CH(NH2)-COOH · HCl | 200 | 182 |
| Comparative Example 2 | A-8 | Ph-CH2-CH(NH2)-COOH | 150 | 223 |

| | Raw material 2: Compound (IV-I) to (IV-IV) | | | | |
|---|---|---|---|---|---|
| | Compound | Structural formula | Amount added (g) | Molecular weight | molar ratio |
| Example 45 | B-15 | HO-CH2-CH(NHBoc)-CH2CH3 | 48 | 189 | 4.03 |
| Example 46 | B-16 | BocHN-CH2-CH(OH)-CH2-NHBoc | 35 | 290 | 8.49 |
| Example 47 | B-17 | C(CH2NHBoc)3-OH | 50 | 419 | 8.59 |
| Example 48 | B-18 | C(CH2NHBoc)3-CH2OH | 75 | 433 | 5.92 |
| Comparative Example 1 | B-1 | HO-CH2CH2-NH2 | 70 | 61 | 0.96 |

TABLE 8-continued

| | | | | | | | |
|---|---|---|---|---|---|---|---|
| Comparative Example 2 | B-5 | 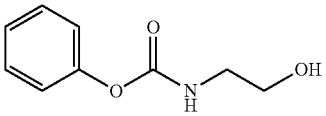 [SMILES: O=C(NCCO)Oc1ccccc1] | | | 120 | 181 | 1.01 |

| | Acid | | Solvent | | Reaction conditions | | |
|---|---|---|---|---|---|---|---|
| Examples | Compound name | Amount added (g) | Compound name | Amount added (g) | Temperature (° C.) | Pressure (kPa) | Time (hr) |
| Example 45 | phosphoric acid | 139 | xylene | 200 | 130 | 40 | 5 |
| Example 46 | phosphoric acid | 139 | xylene | 200 | 130 | 40 | 5 |
| Example 47 | phosphoric acid | 139 | xylene | 200 | 130 | 40 | 5 |
| Example 48 | phosphoric acid | 139 | xylene | 200 | 130 | 40 | 5 |
| Comparative Example 1 | hydrogen chloride | 130 | toluene | 200 | 100 | 80 | 8 |
| Comparative Example 2 | hydrogen chloride | 277 | toluene | 200 | 100 | 80 | 8 |

| | | Product | | Amount of |
|---|---|---|---|---|
| Examples | Compound | Structural formula | Yield (%) | acid in product wt % |
| Example 45 | E-45 | 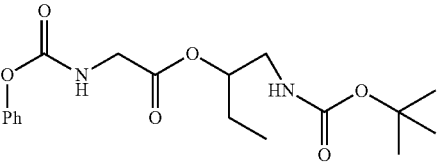 [SMILES: CCC(CNC(=O)OC(C)(C)C)OC(=O)CNC(=O)Oc1ccccc1] | 79 | 0.07 |
| Example 46 | E-46 | 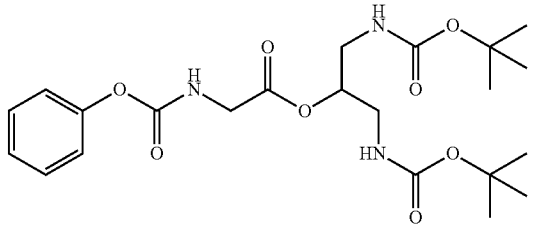 [SMILES: CC(C)(C)OC(=O)NCC(CNC(=O)OC(C)(C)C)OC(=O)CNC(=O)Oc1ccccc1] | 77 | 0.04 |
| Example 47 | E-47 | 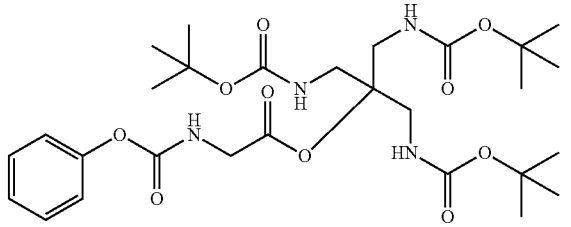 [SMILES: CC(C)(C)OC(=O)NCC(CNC(=O)OC(C)(C)C)(CNC(=O)OC(C)(C)C)OC(=O)CNC(=O)Oc1ccccc1] | 77 | 0.03 |

| Example 48 | E-48 | 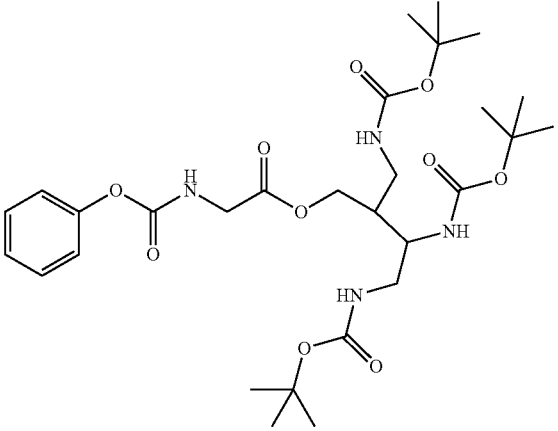 [SMILES: CC(C)(C)OC(=O)NCC(COC(=O)CNC(=O)Oc1ccccc1)C(CNC(=O)OC(C)(C)C)NC(=O)OC(C)(C)C] | 78 | 0.06 |
| --- | --- | --- | --- | --- |
| Comparative Example 1 | E-8 | 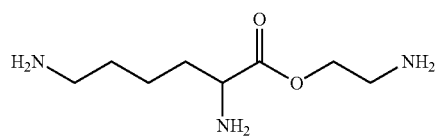 [SMILES: NCCCCC(N)C(=O)OCCN] | 88 | 0.01 |
| Comparative Example 1 | E-10 | 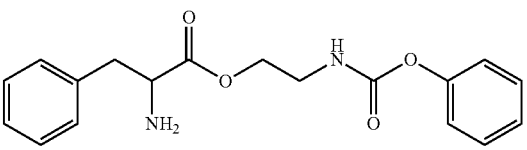 [SMILES: NC(Cc1ccccc1)C(=O)OCCNC(=O)Oc1ccccc1] | 50 | 0.01 |

As is evident from Examples 1 to 48, the yield of every products was at least 67%, with the target product able to be obtained in high yield. Further, the acid was in a liquid state during the production process, and was not contained in the distilled gaseous component.

INDUSTRIAL APPLICABILITY

The production method of an embodiment of the present invention can produce an amino acid aminoalkyl ester or an inorganic acid salt thereof in high yield without acid distillation.

The invention claimed is:

1. A method for producing an amino acid aminoalkyl ester or an inorganic acid salt thereof by reacting:
a compound represented by general formula (I) shown below or a compound represented by general formula (III) shown below, or a salt thereof, and
at least one compound selected from the group consisting of compounds represented by general formula (IV-I) shown below, compounds represented by general formula (IV-II) shown below, compounds represented by general formula (IV-III) shown below and compounds represented by general formula (IV-IV) shown below, or an inorganic acid salt thereof:

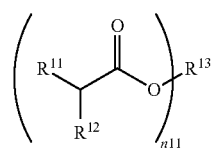

(I)

wherein in general formula (I), $R^{11}$ represents a hydrogen atom, a monovalent aliphatic hydrocarbon group having at least 1 but not more than 10 carbon atoms which may have a substituent, or a monovalent aromatic cyclic group having at least 6 but not more than 10 carbon atoms which may have a substituent; the substituent is a group selected from the group consisting of monovalent aliphatic hydrocarbon groups having at least 1 but not more than 10 carbon atoms, monovalent aromatic cyclic groups having at least 6 but not more than 10 carbon atoms, groups represented by general formula (II-1) shown below and groups represented by general formula (II-2) shown below; $R^{12}$ represents a group selected from the group consisting of groups represented by general formula (II-1) shown below and groups represented by general formula (II-2) shown below; $R^{13}$ represents a hydrogen atom; and n11 is 1,

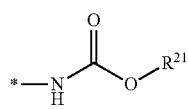

(II-1)

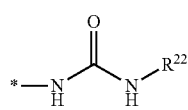

(II-2)

wherein in general formula (II-1), $R^{21}$ represents a monovalent aliphatic hydrocarbon group having at least 1 but not more than 10 carbon atoms which may have a substituent, or a monovalent aromatic cyclic group having at least 6 but not more than 10 carbon atoms which may have a substituent; and in general formula (II-2), $R^{22}$ represents a monovalent organic group;

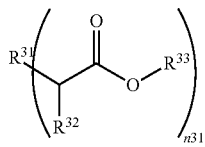 (III)

wherein in general formula (III), n31 is an integer of at least 2 but not more than 4; $R^{31}$ represents an n31-valent aliphatic hydrocarbon group having at least 1 but not more than 10 carbon atoms which may have a substituent, or an n31-valent aromatic cyclic group having at least 6 but not more than 10 carbon atoms which may have a substituent; the substituent is a group selected from the group consisting of monovalent aliphatic hydrocarbon groups having at least 1 but not more than 10 carbon atoms, monovalent aromatic cyclic groups having at least 6 but not more than 10 carbon atoms, groups represented by the general formula (II-1), groups represented by the general formula (II-2), groups represented by the general formula (II-3), and groups represented by the general formula (II-4); $R^{32}$ represents a group selected from the group consisting of groups represented by the general formula (II-1), groups represented by the general formula (II-2) and groups represented by the general formula (II-3); and $R^{33}$ represents a hydrogen atom or a monovalent organic group,

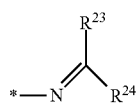 (II-3)

wherein in general formula (II-3), each of $R^{23}$ and $R^{24}$ independently represents a monovalent aliphatic hydrocarbon group having at least 1 but not more than 10 carbon atoms which may have a substituent, or a monovalent aromatic cyclic group having at least 6 but not more than 10 carbon atoms which may have a substituent; and

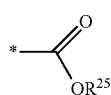 (II-4)

wherein in general formula (II-4), $R^{25}$ represents a hydrogen atom or a monovalent organic group,

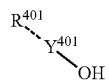 (IV-I)

wherein in general formula (IV-I), $Y^{401}$ represents a divalent aliphatic hydrocarbon group having at least 1 but not more than 10 carbon atoms or a divalent aromatic cyclic group having at least 6 but not more than 10 carbon atoms; and $R^{401}$ represents a group selected from the group consisting of an amino group, —NHCONH$_2$, groups represented by the general formula (II-1), groups represented by the general formula (II-2), and groups represented by the general formula (II-3),

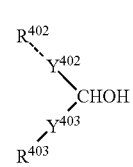 (IV-II)

wherein in general formula (IV-II), each of $Y^{402}$ and $Y^{403}$ independently represents a divalent aliphatic hydrocarbon group having at least 1 but not more than 10 carbon atoms or a divalent aromatic cyclic group having at least 6 but not more than 10 carbon atoms; and each of $R^{402}$ and $R^{403}$ independently represents a group selected from the group consisting of a hydrogen, an amino group, —NHCONH$_2$, groups represented by the general formula (II-1), groups represented by the general formula (II-2), and groups represented by the general formula (II-3), provided that $R^{402}$ and $R^{403}$ do not simultaneously represent a hydrogen,

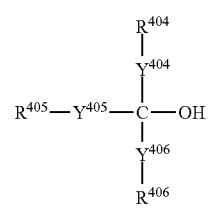 (IV-III)

wherein in general formula (IV-III), each of $Y^{404}$, $Y^{405}$ and $Y^{406}$ independently represents a divalent aliphatic hydrocarbon group having at least 1 but not more than 10 carbon atoms or a divalent aromatic cyclic group having at least 6 but not more than 10 carbon atoms; and each of $R^{404}$, $R^{405}$ and $R^{406}$ independently represents at I act one a group selected from the group consisting of a hydrogen, an amino group, —NHCONH$_2$, groups represented by the general formula (II-1), groups represented by the general formula (II-2), and groups represented by the general formula (II-3), provided that $R^{404}$, $R^{405}$ and $R^{406}$ do not simultaneously represent a hydrogen,

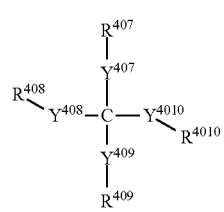 (IV-IV)

wherein in general formula (IV-IV), each of $Y^{407}$, $Y^{408}$, $Y^{409}$ and $Y^{4010}$ represents a divalent aliphatic hydrocarbon group having at least 1 but not more than 10 carbon atoms or a divalent aromatic cyclic group having at least 6 but not more than 10 carbon atoms; at least one of $R^{407}$, $R^{408}$, $R^{409}$ and $R^{4010}$ represents a hydroxyl group, and each of the others represents a group selected from the group consisting of a hydrogen, an amino group, —NHCONH$_2$, groups represented by the general formula (II-1), groups represented by the general formula (II-2), and groups represented by the general formula (II-3), provided that $R^{407}$, $R^{408}$, $R^{409}$ and $R^{4010}$ do not simultaneously represent a hydrogen, wherein the reaction is conducted in presence of at least one acid catalyst selected from the group consisting of organic acids and inorganic acids having a normal boiling point of 0° C. or higher, and the inorganic acid used as an acid catalyst is at least one acid selected from the group consisting of sulfuric acid, phosphoric acid, nitric acid and boric acid.

2. The method according to claim 1, wherein the salt of the compound represented by general formula (I) or general formula (III) is obtained from an acid, which is the same as the acid catalyst.

3. The method according to claim 1, wherein the compound represented by general formula (I) or the compound represented by general formula (III), or a salt thereof, is reacted with the compound represented by general formula (IV-I) or an inorganic acid salt thereof.

4. The method according to claim 3, wherein in the general formula (I):
- $R^{11}$ represents a hydrogen atom or a monovalent aliphatic hydrocarbon group having at least 1 but not more than 10 carbon atoms which may have a substituent,
- the substituent is a group represented by the general formula (II-1),
- $R^{12}$ is a group represented by the general formula (II-1), and
- $R^{13}$ is a hydrogen atom; and in the general formula (IV-I):
- $Y^{401}$ is a divalent aliphatic hydrocarbon group having at least 1 but not more than 10 carbon atoms, and
- $R^{401}$ is a group represented by the general formula (II-1).

5. The method according to claim 1, wherein the acid catalyst is included in an amount of 3 to 80% by mass relative to a total mass of the reaction liquid.

* * * * *